United States Patent
Wang et al.

(10) Patent No.: US 9,518,295 B2
(45) Date of Patent: Dec. 13, 2016

(54) HIGH-THROUGHPUT SEQUENCING METHOD FOR METHYLATED DNA AND USE THEREOF

(75) Inventors: Yan Wang, Beijing (CN); Mingzhi Ye, Shenzhen (CN); Xu Han, Shenzhen (CN); Xiuqing Zhang, Shenzhen (CN); Zhongsheng Sun, Beijing (CN)

(73) Assignees: Institute of Psychology, Chinese Academy of Sciences, Beijing (CN); BGI Shenzhen Co., Ltd., Shenzhen, Guangdong (CN)

( * ) Notice: Subject to any disclaimer, the term of this patent is extended or adjusted under 35 U.S.C. 154(b) by 0 days.

(21) Appl. No.: 13/814,925

(22) PCT Filed: Aug. 11, 2010

(86) PCT No.: PCT/CN2010/001219
§ 371 (c)(1),
(2), (4) Date: Feb. 7, 2013

(87) PCT Pub. No.: WO2012/019320
PCT Pub. Date: Feb. 16, 2012

(65) Prior Publication Data
US 2013/0244885 A1    Sep. 19, 2013

(51) Int. Cl.
*C12Q 1/68* (2006.01)
*C12N 15/10* (2006.01)

(52) U.S. Cl.
CPC ......... *C12Q 1/6874* (2013.01); *C12N 15/1093* (2013.01); *C12Q 1/6804* (2013.01); *C12Q 1/6806* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 2003/0129602 A1* | 7/2003 | Huang | 435/6 |
| 2005/0196792 A1* | 9/2005 | Fodor et al. | 435/6 |
| 2006/0292611 A1* | 12/2006 | Berka et al. | 435/6 |
| 2009/0148842 A1* | 6/2009 | Gormley et al. | 435/6 |

FOREIGN PATENT DOCUMENTS

WO    WO 2007010004    1/2007

OTHER PUBLICATIONS

Cokus et al. Nature 452.7184 (2008): 215-219 and supplementary materials.*

Lister et al. (Finding the fifth base: Genome-wide sequencing of cytosine methylation, Genome Res. Jun. 2009;19(6):959-66. Epub Mar. 9, 2009).*
Frommer, M. et al, "A genomic sequencing protocol that yields a positive display of 5-methylcytosine residues in individual DNA strands," Proc. Nati. Acad. Sci. USA, vol. 89, pp. 1827-1831 (Mar. 1992), 5 pages.
Herman, J.G. et al, "Methylation-specific PCR: A novel PCR assay for methylation status of CpG islands," Proc. Natl. Acad. Sci. USA, vol. 93, pp. 9821-9826 (Sep. 1996), 6 pages.
Huang, T.H.M. et al., "Methylation profiling of CpG islands in human breast cancer cells," Human Molecular Genetics, vol. 8, No. 3, pp. 459-470 (No month listed 1999), accessed Feb. 21, 2013, 12 pages.
Ruike, Y. et al., "Genome-wide analysis of aberrant methylation in human breast cancer cells using methyl-DNA immunoprecipitation combined with high-throughput sequencing," BMC Genomics, vol. 11, 11 pages (No month listed 2010), 11 pages.
Serre, D. et al, "MBD-isolated Genome Sequencing provides a high-throughput and comprehensive survey of DNA methylation in the human genome," Nucleic Acids Research, vol. 38, No. 2, pp. 391-399 (Nov. 11, 2009), accessed Feb. 20, 2013, 9 pages.
Smiraglia, D.J. et al., "The study of aberrant methylation in cancer via restriction landmark genomic scanning," Oncogene, vol. 21, pp. 5414-5426 (No month listed 2002), 13 pages.
Weber, M. et al, "Chromosome-wide and promotor-specific analyses identify sites of differential DNA methylation in normal and transformed human cells," Nature Genetics, vol. 37, No. 8, pp. 853-862 (Aug. 2005), published online Jul. 10, 2005, 10 pages.
Xiang, H. et al., "Single base-resolution methylome of the silkworm reveals a sparse epigenomic map," Nature Biotechnology Letters, 7 pages (May 2, 2010), 7 pages.
Zeschnigk, M. et al, "Massive parallel bisulfite sequencing of CG-rich DNA fragments reveals that methylation of many X-chromosomal CpG islands in female blood DNA is incomplete," Human Molecular Genetics, vol. 18, No. 8, pp. 1439-1448 (Feb. 17, 2009), accessed Feb. 20, 2013, 10 pages.
International Search Report for International Application No. PCT/CN2010/001219 mailed May 26, 2011. 7 pages.
Harris et al., "Comparison of sequencing-based methods to profile DNA methylation and identification of monoallelic epigenetic modifications," Nature Biotechnology, vol. 28, No. 10, pp. 1097-1108, Oct. 2010.

* cited by examiner

*Primary Examiner* — Angela M Bertagna
(74) *Attorney, Agent, or Firm* — Wilmer Cutler Pickering Hale and Dorr LLP

(57) ABSTRACT

The present invention provides a high-throughput sequencing method for methylated DNA, and use thereof. Particularly, the present invention provides a high-throughput sequencing method for methylated DNA, which combines methylated DNA immunoprecipitation, removal of repetitive sequences, and bisulfite treatment. The site of sequencing library will be decreased, and the cost will be reduced by using the method disclosed in the present invention.

7 Claims, 15 Drawing Sheets

SEQUENCE LISTING

```
<160> NUMBER OF SEQ ID NOS: 8

<210> SEQ ID NO 1
<211> LENGTH: 29
<212> TYPE: DNA
<213> ORGANISM: artificial sequence
<220> FEATURE:
<223> OTHER INFORMATION: auxiliary adapter

<400> SEQUENCE: 1
agctgggcac cgctcatgcc actccggct                                        29

<210> SEQ ID NO 2
<211> LENGTH: 26
<212> TYPE: DNA
<213> ORGANISM: artificial sequence
<220> FEATURE:
<223> OTHER INFORMATION: auxiliary adapter

<400> SEQUENCE: 2
gccggagtgg catgagcggt gcccag                                           26

<210> SEQ ID NO 3
<211> LENGTH: 33
<212> TYPE: DNA
<213> ORGANISM: artificial sequence
<220> FEATURE:
<223> OTHER INFORMATION: auxiliary adapter primer

<400> SEQUENCE: 3
ggtcagcagc taaacaccac tcataccact cca                                   33

<210> SEQ ID NO 4
<211> LENGTH: 35
<212> TYPE: DNA
<213> ORGANISM: artificial sequence
<220> FEATURE:
<223> OTHER INFORMATION: auxiliary adapter primer

<400> SEQUENCE: 4
ggtcagcagt tgggtattgt ttatgttatt ttggt                                 35

<210> SEQ ID NO 5
<211> LENGTH: 32
<212> TYPE: DNA
<213> ORGANISM: artificial sequence
<220> FEATURE:
<223> OTHER INFORMATION: auxiliary adapter
<220> FEATURE:
```

```
<221> NAME/KEY: modified_base
<222> LOCATION: (31)..(31)
<223> OTHER INFORMATION: m5c

<400> SEQUENCE: 5
ctgggcaccg ctcatgccac tccggctaag ct                              32

<210> SEQ ID NO 6
<211> LENGTH: 31
<212> TYPE: DNA
<213> ORGANISM: artificial sequence
<220> FEATURE:
<223> OTHER INFORMATION: auxiliary adapter
<220> FEATURE:
<221> NAME/KEY: modified_base
<222> LOCATION: (2)..(2)
<223> OTHER INFORMATION: m5c

<400> SEQUENCE: 6
gcttagccgg agtggcatga gcggtgccca g                               31

<210> SEQ ID NO 7
<211> LENGTH: 24
<212> TYPE: DNA
<213> ORGANISM: artificial sequence
<220> FEATURE:
<223> OTHER INFORMATION: auxiliary adapter primer

<400> SEQUENCE: 7
ctaaacacca ctcataccac tcca                                       24

<210> SEQ ID NO 8
<211> LENGTH: 26
<212> TYPE: DNA
<213> ORGANISM: artificial sequence
<220> FEATURE:
<223> OTHER INFORMATION: auxiliary adapter primer

<400> SEQUENCE: 8
ttgggtattg tttatgttat tttggt                                     26
```

US 9,518,295 B2

HIGH-THROUGHPUT SEQUENCING METHOD FOR METHYLATED DNA AND USE THEREOF

RELATED APPLICATIONS

This application is a national stage of International Application No. PCT/CN2010/001219 filed Aug. 11, 2010, the contents of which are incorporated by reference herein in their entirety.

TECHNICAL FIELD

The present invention belongs to the fields of genomics and biotechnology. In particular, it relates to a high-throughput sequencing method for precisely identifying methylation status of 5' carbon atom of cytosine in functional region of genome by combining methylated DNA immunoprecipitation, removal of repetitive sequences and bisulfate treatment; and it further provides a device for carrying out the sequencing method, whereby the sequencing cost is reduced, amount of information processing is reduced, and high-throughput sequencing of methylated DNA is more efficiently carried out.

BACKGROUND OF INVENTION

Relationship Between DNA Methylation and Gene Modulation or Diseases

In higher eukaryote genome, DNA methylation allows changes in spatial structure of modified DNA to lead to gene silencing or overexpression without altering type and number of DNA bases, whereby various phenotypes in organisms are rendered.

For instance, methylation usually occurs at the CpG sites in normal cells, while methylation does not occur in CpG islands in promoters. The whole level of DNA methylation in tumor cells is significantly reduced, and significant demethylation occurs in regions with low gene abundance. This low level of DNA methylation results in chromosomal instability and carcinogenesis. For example, testicle-specific genes, melanoma-associated genes, and proliferation related genes are silenced in somatic cells, and the CpG islands of promoters thereof are methylated; while demethylation occurs in promoters of corresponding cancer cells, such that these genes can be expressed. In addition, reduced level of methylation promotes expression of some genes (e.g., transcription factors related to proliferation). During development of tumors, the reduction in level of DNA methylation will result in further worsening of damage, inducing transformation from benign proliferation to malignant proliferation.

DNA methylation plays a very important role in gene expression pattern and genome stability. In view that most of the researchers in the world have recognized that DNA methylation plays an important role in onset and development of human disease and DNA methylation has become one of the research focuses at present, and DNA methylation modification acts on whole genome, techniques for detecting DNA methylation have influences on the studies and understandings of methylation, thereby affecting the studies on human disease, in particular the cancers to a great extent.

Current Sequencing Methods for DNA Methylation

Now, according to different methods of preparing the sequencing libraries, the existing sequencing techniques for detecting DNA methylation may be divided into, shotgun bisulfite sequencing, MeDIP sequencing, MBD sequencing, enzymatic digestion-bisulfite sequencing and so on.

Shotgun Bisulfite Sequencing Method

Shotgun bisulfite sequencing method comprises mainly the following steps: DNA fragmentation, end repairing of DNA fragments, methylated sequencing adapter addition, bisulfite treatment, PCR amplification, sequencing and sequencing data alignment. In details, the fragmented DNA, after subjecting to end modification and addition of "A" base to 3'-end, is directly linked to a methylated sequencing adapter (all sites in the adapter are modified as methylation status); unmethylated cytosines in single-stranded DNA are deaminated by bisulfite under appropriate reaction conditions to give uracils while leaving methylated cytosines unchanged, i.e., bisulfite treatment occurs. Then PCR amplification is carried out to convert all the uracils to the thymines. Finally, the PCR products are sequenced and are compared with untreated sequences to determine whether methylation occurs at CpG sites.

This sequencing method has been applied in sequencing Arabidopsis methylation and human cell line, and billions of sequencing data are obtained with sequencing depth of 20× and 14×, respectively, that is, the average sequencing depth for the whole genome is up to 20 times and 14 times, respectively.

Although this sequencing method has solved the issue associated with high-throughput scanning of DNA methylation patterns on a whole-genome level, this method produces huge number of nucleotide sequences, resulting in the following new problems. The first problem is analysis of huge number of data, in particular, analysis of sequencing data of a large genome of higher mammals (there are about 60 billions base pairs for 20× coverage). After sequencing, it needs great and complex works to perform splicing and alignment of huge number of data. The second problem is the sequencing cost. Even if the newest 3G sequencing chip is used in this method, the sequencing cost is still very expensive. Thus this method cannot be served as a conventional experimental technique adapted to most molecular biological laboratories.

MeDIP Sequencing and MBD Sequencing

Since methylation in mammal generally occurs in the 5' carbon atom of cytosine of CpG, it is possible to enrich highly methylated DNA fragments by protein (MBD) or 5'-methylcytosine antibody (MeDIP) that specifically binds to methylated DNA. The enriched DNA fragments are sequenced by high-throughput sequencing. Specifically, a method for isolating methylated DNA fragments by MBD method is called as methylation CpG immunoprecipitation (MCIp). MeDIP consists in that 5-methylcytosine antibody can be used for immuneprecipitating enriched methylated DNA fragments with high specificity, and 5-methylcytosine antibody can also bind to single methylated cytosine at non-CpG site. Therefore, it has higher specificity than MBD. This technique is called as methylated DNA immunoprecipitation, which can be used for high throughput screening of abnormal methylated genes in combination with new generation sequencing technique. The method avoids the limitations of enzyme cutting site when restriction enzymes are used.

When MeDIP sequencing or MBD sequencing is carried out, a sequencing library needs to be prepared. Genomic DNA is fragmented and then linked to sequencing adapters that are not chemically modified. Then DNA fragments containing methylated cytosine are separated from unmethylated DNA fragments with MBD or 5-methylcytosine antibody. The methylated DNA fragments are purified and directly subjected to PCR and sequencing without bisulfite treatment.

For instance, HCT116 colon cancer cell line DNA was sequenced via MBD method by David Serre, and the results showed that about 19 millions (occupying two channels of chip) of sequencing data can detect all known methylated or some unknown methylated regions, largely lowering sequencing cost. However, since there is no bisulfite treatment before sequencing, it is necessary to identify methylated CpG sites to distinguish them, which markedly increases subsequent work.

Enzymatic Digestion-Bisulfite Sequencing

Enzymatic digestion-bisulfite sequencing aims at enriching DNA fragments to be detected, reducing size of sequencing library and lowering sequencing cost. The technique is able to successfully enrich some CpG islands (different CpG islands are obtained by alignment of 8% of the data). The technique reduces the size of sequencing library to some extent. It is not necessary to carry out subsequent identification of methylation sites after bisulfite treatment.

For instance, DNA fragments in CpG rich regions were enriched with 4 endonucleases when bisulfite sequencing based on enzymatic digestion was employed by Michael Zeschnigk [Smiraglia D J, Plass C. The study of aberrant methylation in cancer via restriction landmark genomic scanning. Oncogene 2002; 21: 5414-5426]. The principle of the method is that the fragmentation of DNA is not achieved by ultrasound but achieved by combined enzymatic digestion by multiple endonucleases (MseI, Tsp 509I, NlaIII and Hpy CH4V), wherein the restriction enzyme cutting sites of MseI, Tsp509I, NlaIII and Hpy CH4V are TTAA, AATT, CATG and TGCA, respectively. According to computer prediction made by the authors, the combined enzymatic digestion by these four enzymes is superior to the combined enzymatic digestion by other enzymes in terms of DNA fragment sizes and number of CpG islands that can be cleaved, etc. After enzymatic digestion, fragments of 300 bp-800 bp were purified, linked to methylated sequencing adapters, subjected to bisulfite treatment and PCR, and sequenced.

However, since the genomic DNA is digested by restriction enzymes in this technique, and the restriction enzyme cutting sites are fixed, the distribution of fragment size differs greatly. DNAs of less than 300 bp or greater than 800 bp are given up so that a part of genomic DNA cannot be sequenced. In addition, since the reading length of sequencer is only 130 bp, fragments of 300 bp-800 bp cannot be sequenced through. Hence, a part of methylated DNA fragments having biological sense and function cannot be detected by this technique.

No matter which of the above techniques is used, there is a noteworthy problem. That is, sequencing by all the above techniques will produce a huge number of sequencing data with no biological function. This is because, in the existing methods of library construction and sequencing, data of heterochromatin regions consisting of a huge number of repetitive sequences accounts for a high proportion of the sequencing data. This is due to the fact that genes to be detected comprise repetitive sequences of highly methylated CpGs (for example, centromeres and telomeres comprise repetitive sequences, in particular, highly repetitive sequences, and these repetitive sequences are believed to involve in structure and composition of chromosomes, while it has not been found that they directly take part in expression and regulation of genes). However, the analysis of relationship between the DNA methylation of repetitive sequences, especially highly repetitive sequence and the expression of target genes is weaker [Herman J G et al., Methylation—specific PCR: a novel PCR assay for methylation status of CpG islands. Proc Natl Acad Sci USA 1996; 93: 9821-9826]. Therefore, by removing the repetitive sequences and only sequencing the methylated DNA fragments in the functional regions will make the cost significantly reduce.

Techniques for Removing Repetitive Sequences

The researchers have studied how to remove repetitive sequences at present. For example, bisulfite sequencing technique is combined with high density chips, wherein the scope of target methylated DNA is selected by chip hybridization. It is known that chip probes designed by Agilent and NimbleGen are centered in promoters and first exon of genome which can remove, such as, redundancy from heterochromatin DNA fragments. In addition, detection of single base polymorphisms based on high throughput sequencing technique also utilizes exon capturing chips to capture exon DNA fragments to reduce size of sequencing library, thereby lowering sequencing cost for each sample. However, the quantity of DNA captured by exon capturing chips is limited, affecting the subsequent experiments, and its ability to remove redundant methylated DNA is not enough to satisfy sequencing analysis of methylated DNA at genome level.

As is known, C0T-1 DNAs are applied as blocking sequences for repetitive sequences in hybridization tests such as fluorescence in-situ hybridization and comparative genomic hybridization etc. The inventors believe that it may be used as an important tool to remove repetitive sequences. It is known that C0T-1 DNA is rich in highly and moderately repetitive sequences, and is produced based on the principle that denatured highly and moderately repetitive sequences can be renatured while single or low copy DNA sequences are difficult to be renatured.

A conventional method for removing C0T-1 DNA repetitive sequences is described as follows: C0T-1 DNA is labeled with biotin. Magnetic beads are coated with avidin. The C0T-1 DNA labeled with biotin is bound to the magnetic beads coated with avidin by utilizing the principle that avidin binds to biotin to obtain a complex of C0T-1 DNA labeled with biotin and magnetic beads coated with avidin. The complexes are hybridized with target DNA fragments that might comprise repetitive sequences. Based on the principle that denatured highly and moderately repetitive sequences can be renatured while single or low copy DNA sequences are difficult to be renatured, the repetitive sequences are hybridized with the C0T-1 DNA labeled with biotin to obtain a complex containing the repetitive sequences—C0T-1 DNA labeled with biotin—magnetic beads coated with avidin. The magnetic bead complexes are separated and discarded. Meanwhile, the target DNA that has been treated by magnetic beads is recovered. The recovered DNA is a DNA fragment from which the repetitive sequences have been removed.

Removal of repetitive sequences by C0T-1 DNA is characterized in that methylated DNA fragments in the functional regions (promoters, exons, and a part of introns) will not be captured and removed, while highly and moderately methylated repetitive sequences in the heterochromatin regions are removed. This method for removing repetitive sequences can satisfy the requirements in sequencing methylated DNA at genome level.

SUMMARY OF THE INVENTION

Confronted with the disadvantages existing in the art, the inventors envisage that redundant methylated sequences are removed by pretreatment and then sequencing is carried out, whereby quantity of information is reduced in subsequent processes, and sequencing cost is lowered. After selection and investigation in many aspects, the inventors design the following technical route for the first time:

(1) methylated DNA fragments are enriched by MeDIP or MBD technique from DNA to be detected;

(2) the enriched methylated DNA fragments in (1) are treated by technique of removing repetitive sequences via C0T-1 DNA to obtain a DNA library that is free of redundant sequences and only comprises methylated DNA fragments in the functional regions;

(3) the library obtained in (2) is subjected to a high throughput sequencing after bisulfite treatment.

In the route, the technique for removing repetitive sequences with C0T-1 DNA is firstly applied in a high throughput sequencing technique.

However, more technical problems appeared when the route is practically applied. The most critical technical problem is matching and linking of the sequencing adapters.

At present, methylated adapters are employed in the bisulfite sequencing technique for methylated DNA. Since all cytosine sites of the adapters are methylated, after a DNA fragment is linked to the methylated sequencing adapter and subjected to bisulfite treatment, the sequence of the adapter does not change, and still matches with sequencing primer after PCR.

However, if MeDIP technique is combined with bisulfite sequencing technique, there are several situations, as follows. (1) Bisulfite sequencing first and then MeDIP treatment is carried out. When the bisulfite sequencing library is constructed, if a methylation modified adapter is introduced prior to sulfonation with bisulfite, the introduction of the methylated adapter will result in "false positive" enrichment of methylated DNA in the subsequent methylation DNA immunoprecipitation (MeDIP). (2) MeDIP sequencing first, and then bisulfite sequencing is carried out and an adapter is not added prior to the MeDIP treatment. Double-stranded DNA will turn to single-stranded DNA after MeDIP which will make the conventional sequencing adaptors difficult to be added. (3) MeDIP sequencing first and then bisulfite sequencing is carried out. If an unmethylated adapter is linked prior to the MeDIP, bisulfite treatment will result in changes of the sequence of adapters, and thus being unmatched with the sequencing primers.

In order to achieve combination of the above two technique for enriching methylated DNA and the technique for bisulfite sequencing methylated DNA, the inventors solve the problems by rationally designing auxiliary adapters and primers, linking and removing of the auxiliary adapters, and the order of the various steps. Thereby, the inventors firstly provide a high throughput sequencing method comprising methylated DNA immunoprecipitation, repetitive sequences removal and bisulfite treatment (MeDIP-repetitive elements removal-bisulfite, hereinafter referred to as MRERB technique). This method satisfies the requirement in detection of target DNA fragments, reduces size of sequencing library of each sample, and decreases data analysis in subsequent processing, thereby lowering sequencing cost. The purpose of mapping of methylation profile of methylated DNA fragments in functional regions at a low cost will be fulfilled.

Specifically, the present invention provides the following contents:

1. A high-throughput sequencing method for methylated DNA, comprising library-constructing step and sequencing step, wherein the library-constructing step refers to a step of obtaining a library of methylated DNA to be detected, and the library-constructing step comprises:

A) fragmentation of genomic DNA and end repairing of double-stranded DNA fragments;

B) linkage of auxiliary adapters to the double-stranded DNA obtained in A), said adapters refers to double-stranded DNA sequence designed to be capable of linking to the end of the repaired double-stranded DNA, and capable of allowing a single-stranded DNA treated by sulfonation to be converted into a double-stranded DNA after PCR, wherein the end of auxiliary adapter that links to the repaired double-stranded DNA is a joining end, the other end is a non-joining end;

C) methylation immunoprecipitation of the product obtained in B);

D) removal of moderately and highly repetitive sequences from the product obtained in C);

E) bisulfite treatment of the product obtained in D);

F) amplification of the single-stranded DNA obtained in E) via a primer (which is designed according to the auxiliary adapter sequence) to obtain a double-stranded DNA;

G) removal of auxiliary adapter by enzymatic digestion;

wherein the sequencing step refers to sequencing of the library obtained in the above mentioned library-constructing steps, and comprises the steps of:

H) end repairing of the double-stranded DNA obtained in G), and linkage of sequencing adapters;

J) DNA sequencing of the product obtained in H).

2. The sequencing method according to the above item 1:

wherein, the auxiliary adapter in the step B) is selected from at least one of the following a-h:

a). an adapter that is free of restriction enzyme cutting site and has a non-joining end being a overhang structure and a joining end being a blunt end;

b). an adapter that comprises restriction enzyme cutting sites and has a non-joining end being a overhang structure and a joining end being a blunt end;

c). an adapter that is free of restriction enzyme cutting site and has a non-joining end being a forked structure and a joining end being a blunt end;

d). an adapter that comprises restriction enzyme cutting sites and has a non-joining end being a forked structure and a joining end being a blunt end;

e). an adapter that is free of restriction enzyme cutting site and has a non-joining end being a overhang structure and a joining end being a sticky end;

f). an adapter that comprises restriction enzyme cutting sites and has a non-joining end being a overhang structure and a joining end being a sticky end;

g). an adapter that is free of restriction enzyme cutting site and has a non-joining end being a forked structure and a joining end being a sticky end;

h). an adapter that comprises restriction enzyme cutting sites and has a non-joining end being a forked structure and a joining end being a sticky end.

The auxiliary adapter in the step B), the primer in the step F) and the digestion enzyme in the step G) are designed as follows:

When an auxiliary adapter is a) or c), the primer is designed to be complementary to the sequence of auxiliary adapter after conversion in E) and to have recognition sites of restriction enzyme additionally attached to the 5'-end, wherein the restriction enzyme cutting site are located on the primer, and the restriction enzyme cutting site are assured to locate within 5 bp of the upstream and downstream of the linking site of the auxiliary adapter to the DNA to be detected; said restriction enzyme is selected from EcoP15I and MmeI. When step G) is carried out, single enzymatic digestion is performed using an enzyme corresponds to the designed restriction enzyme cutting site;

When an auxiliary adapter is b) or d), a restriction enzyme cutting site is designed to locate within 5 bp of upstream of the linking site of the auxiliary adapter to the DNA to be detected. The restriction enzyme cutting site is required to have the following three characteristics: (1) the restriction enzyme cutting site comprises at least one methylated cytosine; (2) the restriction enzyme cutting site does not comprise unmethylated cytosine; and (3) the restriction enzyme cutting site does not comprise CpG dinucleotide site. The restriction enzyme is selected from AluI, BclI, BfaI, BglII, BsrGI, BspHI, CviAII, FatI, HindIII, HpyCH4V, NlaIII, NsiI, PciI, ScaI, SpeI, XbaI, or the like. The primer is designed to be complementary to the sequence of auxiliary adapter after conversion in E). When the step G) is carried out, a single enzymatic digestion is performed using the enzyme corresponds to the designed methylated restriction enzyme cutting site; or another restriction enzyme cutting site is designed on the 5'-end of the primer, and the two restriction enzyme cutting sites are overlapped by adjusting the length of the auxiliary adapter; when the step G) is carried out, a double enzymatic digestion is performed using enzymes correspond to the designed restriction enzyme cutting sites.

When an auxiliary adapter is e) or g), the design principle of the auxiliary adapter and primer is same as that in the solution wherein an auxiliary adapter is a) and c), and the difference between them only resides in linkage manner to target DNA fragment, that is, the linkage manner for a) and c) is "T-A" linkage, while for e) and g) is sticky end linkage. The design principles of auxiliary adapter and primer are not described again.

When an auxiliary adapter is f) or h), the design principle of the auxiliary adapter and primer is same as that in the solution wherein an auxiliary adapter is b) and d), and the difference between them only resides in linkage manner to target DNA fragment, that is, the linkage manner for b) and d) is "T-A" linkage, while for f) and h) is sticky end linkage. The design principles of auxiliary adapter and primer are not described again.

3. The sequencing method according to the item for 2, wherein the step A) comprises:
a). fragmenting the genomic DNA into double-stranded DNA fragments;
b). end repairing of the double-stranded DNA fragments in a) to obtain a blunt end;
c). adding a "A" base to the 3'-end of the blunt end in b).

4. The sequencing method according to item 1 or 2, wherein the methylation immunoprecipitation in step C) is selected from MeDIP and MBD.

5. The sequencing method according to item 1 or 2, wherein the removal of repetitive sequences in step D) is carried out by C0T1 DNA.

6. The sequencing method according to item 2, wherein the restriction enzyme cutting site methylation in step F) refers to b, d, f, h solution, as described above.

7. The sequencing method according to item 1, wherein the auxiliary adapter is designed as a structure for preventing self connection and is labeled with biotin at the 5'-end.

8. An automatic device for carrying out the method according to item 1 or 2.

9. The device according to item 8, which comprises:
A) an element for fragmenting genomic DNA and an element for end repairing;
B) a linkage element for linking the double-stranded DNA obtained in A) to an auxiliary adapter;
C) an element for methylation immunoprecipitation of the product in B);
D) an element for removing moderately and highly repetitive sequences from the product in C);
E) an element for bisulfite treatment of the product in D);
F) an element for PCR amplification of single stranded-DNA obtained in E) via a primer to obtain a double-stranded DNA;
G) an element for removing the auxiliary adapter by enzymatic digestion;
H) an element for end repairing of the double-stranded DNA obtained in G);
J) an element for linking the repaired DNA in H) to a sequencing adapter;
K) a sequencing element for sequencing methylated DNA in the product in J).

g). an adapter that is free of restriction enzyme cutting site and has a non-joining end being a forked structure and a joining end being a sticky end;

h). an adapter that comprises restriction enzyme cutting sites and has a non-joining end being a forked structure and a joining end being a sticky end.

Figure 2:
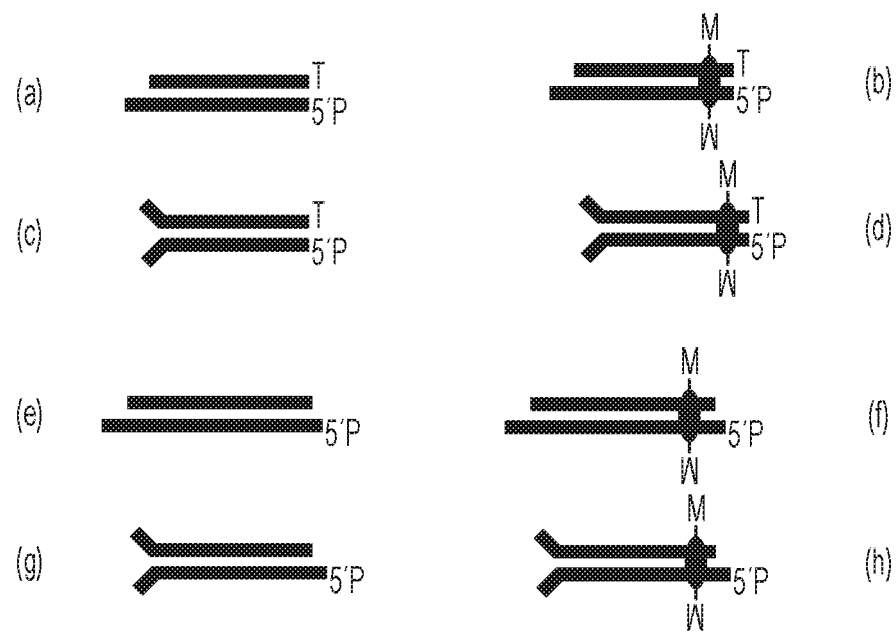
FIG. 2 is design diagram of auxiliary adapter. Auxiliary adapters are divided into two types according to whether or not auxiliary adapters comprise a restriction enzyme cutting site: i.e., auxiliary adapters with restriction enzyme cutting site and auxiliary adapters without restriction enzyme cutting site (b, d, f, h); non-joining end of an auxiliary adapter may be designed into three forms: forked structure (figures c and d), a chain with overhang structure and blunt end structure. The auxiliary adapters can be divided into the following eight types according to the non-joining end and TA linkage of joining end of auxiliary adapter or other sticky linkage characteristics:
a). an adapter that is free of restriction enzyme cutting site and has a non-joining end being a overhang structure and a joining end being a blunt end;
b). an adapter that comprises restriction enzyme cutting sites and has a non-joining end being a overhang structure and a joining end being a blunt end;
c). an adapter that is free of restriction enzyme cutting site and has a non-joining end being a forked structure and a joining end being a blunt end;
d). an adapter that comprises restriction enzyme cutting sites and has a non-joining end being a forked structure and a joining end being a blunt end;
e). an adapter that is free of restriction enzyme cutting site and has a non-joining end being a overhang structure and a joining end being a sticky end;
f). an adapter that comprises restriction enzyme cutting sites and has a non-joining end being a overhang structure and a joining end being a sticky end.
Figure 3:
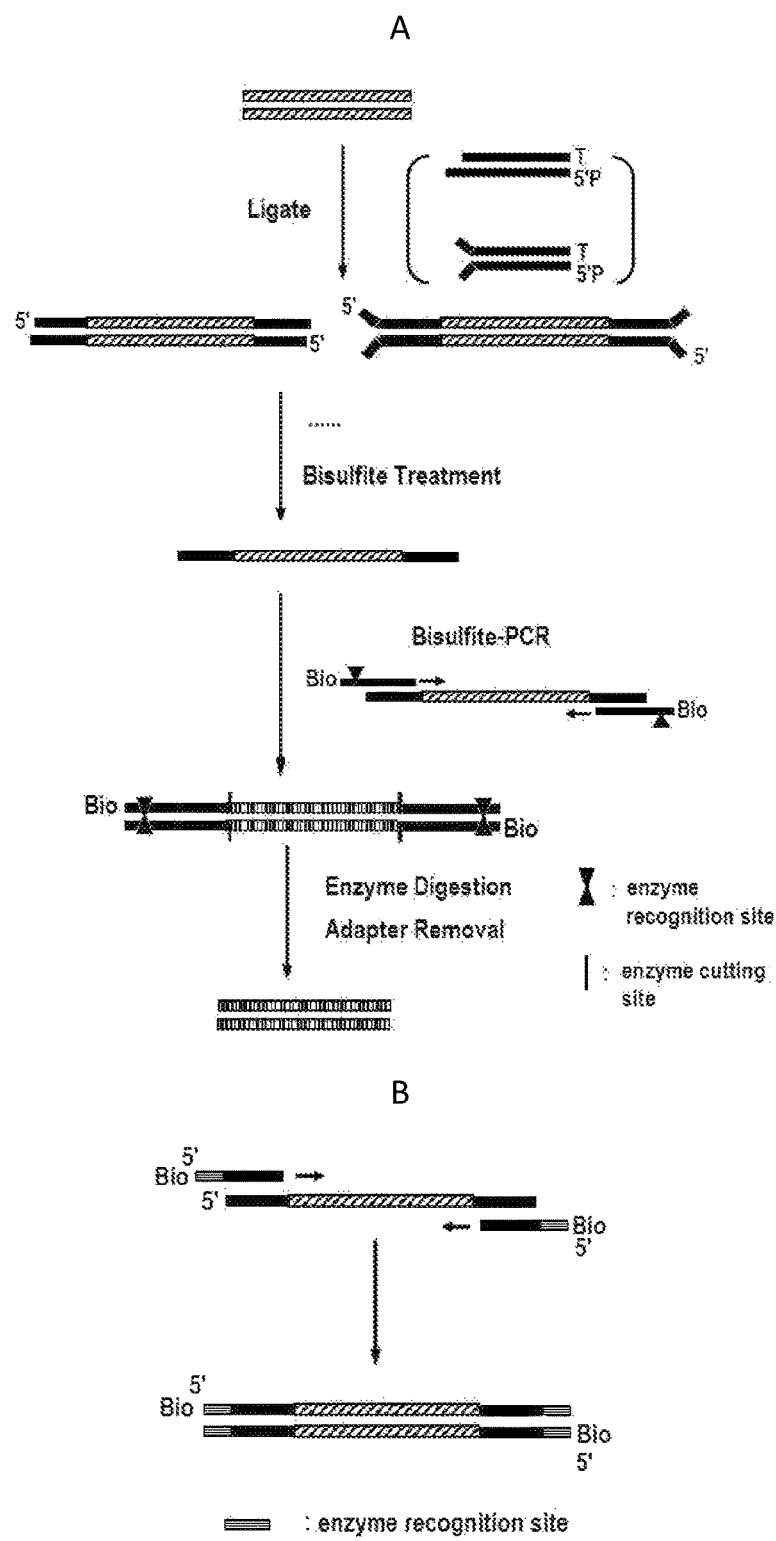

FIG. 3 shows linkage and removal manner (1) of an auxiliary adapter with a blunt end. The a) and c) auxiliary adapters in FIG. 2 are used in this manner. Since the auxiliary adapter 1 is designed to be removed by enzymatic digestion after bisulfite treatment, and the auxiliary adapter 1 to be removed is present at the end of DNA to be detected in the form of single strand, in order to effectively remove the auxiliary adapter 1 and to allow the single-stranded DNA to become a double-stranded DNA at the same time to facilitate linkage of subsequent sequencing adapter, the inventors have designed a primer (A) that matches with the sequence of the auxiliary adapter 1 after bisulfite treatment, and a restriction enzyme recognition site (B) is designed to locate at the position close to the 5'-site of the primer, wherein the restriction enzyme recognition site does not match with the sequence of the auxiliary adapter and is located at the overhang portion of the primer. A restriction enzyme cutting site is selected so as to be adapted to the restriction endonuclease, and the restriction endonuclease is characterized in digesting DNA at 20-30 bp downstream of the restriction enzyme recognition site. The restriction enzyme cutting site is designed to be within 5 bp of the end of DNA fragment to which the auxiliary adapter is linked, by controlling the length of the auxiliary adapter.

Figure 4:
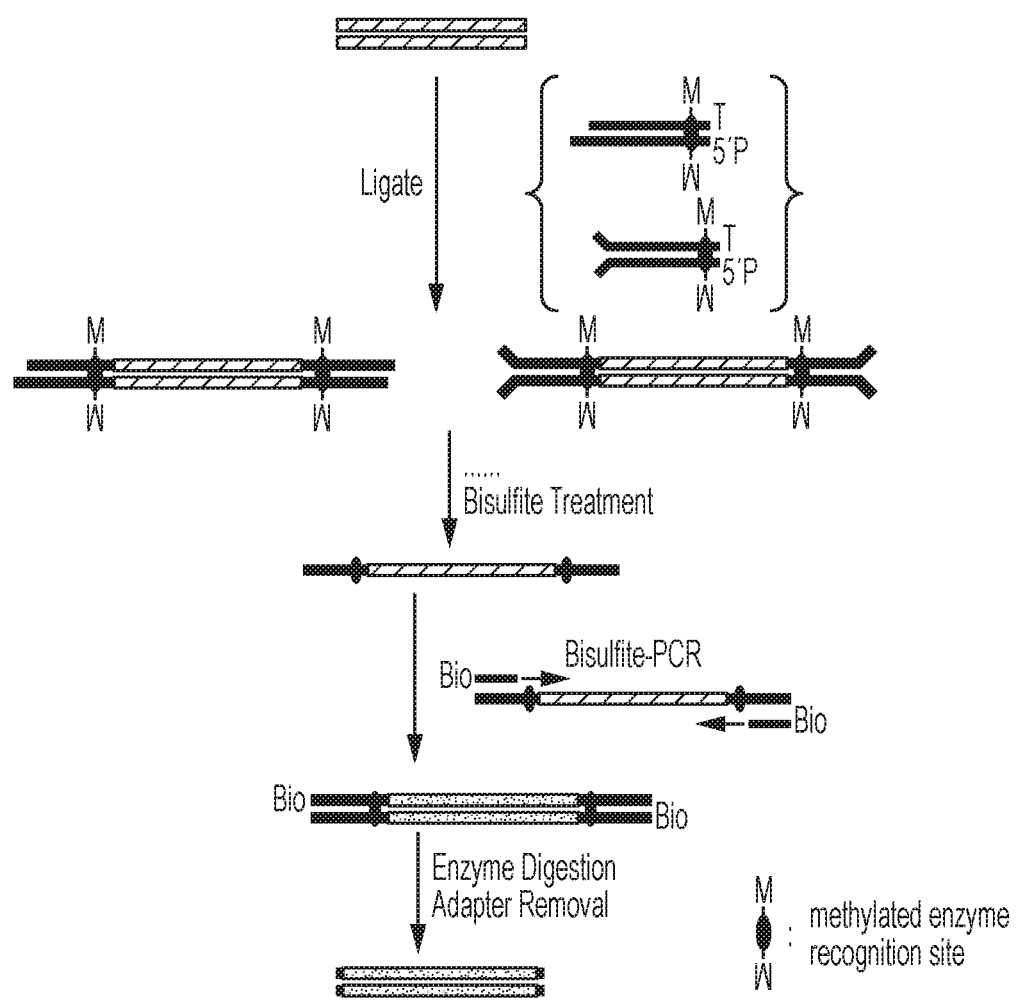

FIG. 4 shows linkage and removal manner (2) of an auxiliary adapter with a blunt end, i.e., the linkage and removal of the auxiliary adapter 1 comprising a methylated restriction enzyme cutting site. The b) and d) auxiliary adapters in FIG. 2 may be used in this manner. The adapter 1 comprises a methylated restriction enzyme cutting site. The methylated restriction enzyme cutting site can assure that the DNA fragments are intact when the auxiliary adapter is removed by means of enzymatic digestion (but damage within 5 bp of the end of the DNA fragments is allowed) and that the restriction enzyme recognition sequence is not changed after bisulfite treatment.

Figure 5:
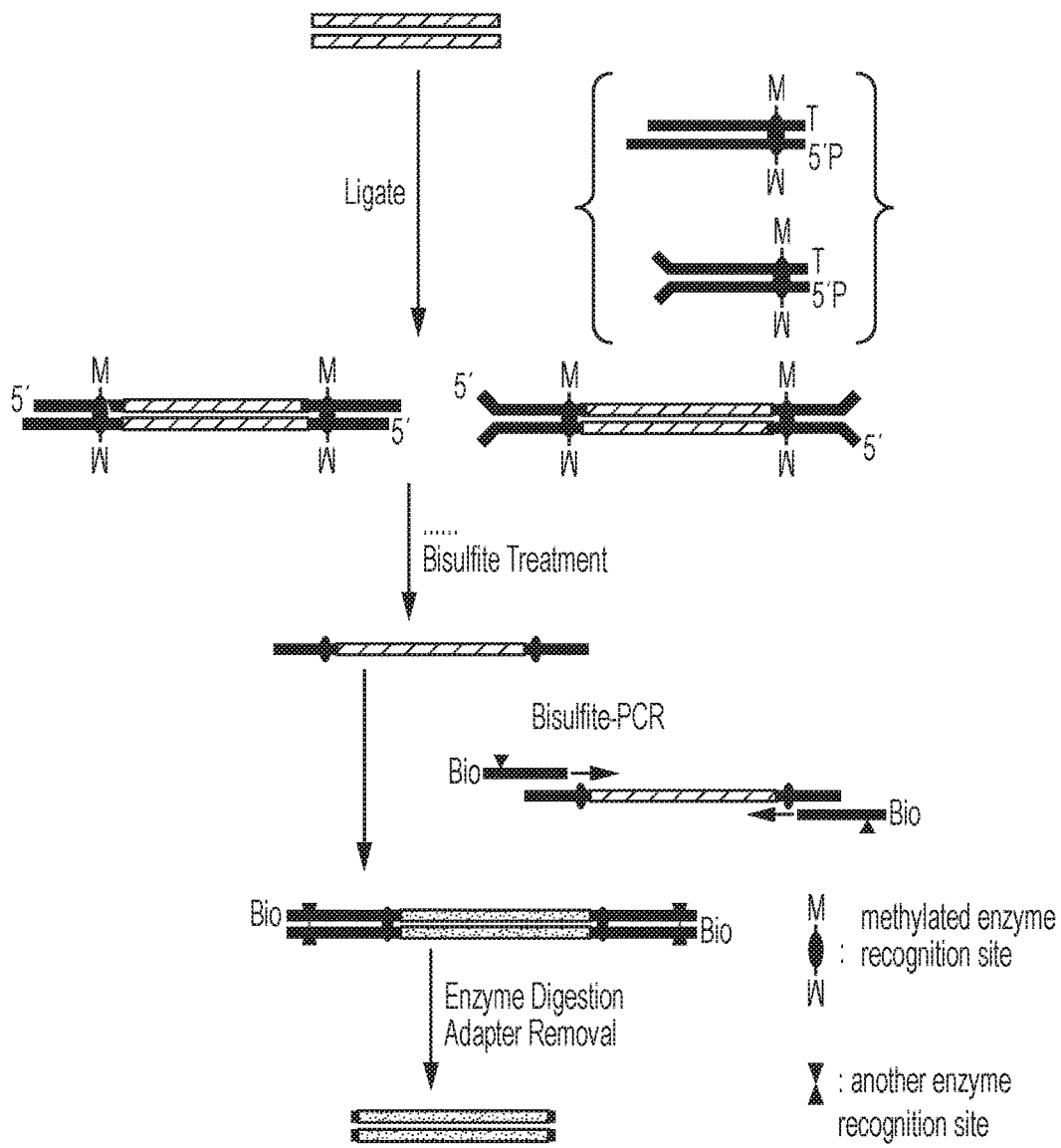

FIG. 5 shows linkage and removal manner (3) of an auxiliary adapter with a blunt end, i.e., the linkage and removal of the auxiliary adapter, wherein the auxiliary adapter comprises a methylated restriction enzyme cutting site and the primer comprises a restriction enzyme cutting site. A restriction enzyme cutting site is similarly designed close to the linkage site of the auxiliary adapter. Another restriction enzyme cutting site is designed at the 5'-end of the primer. The two restriction enzyme sites are overlapped by adjusting the length of the auxiliary adapter. The thoroughness of enzymatic digestion is assured by two enzymatic digestions.

Figure 6:
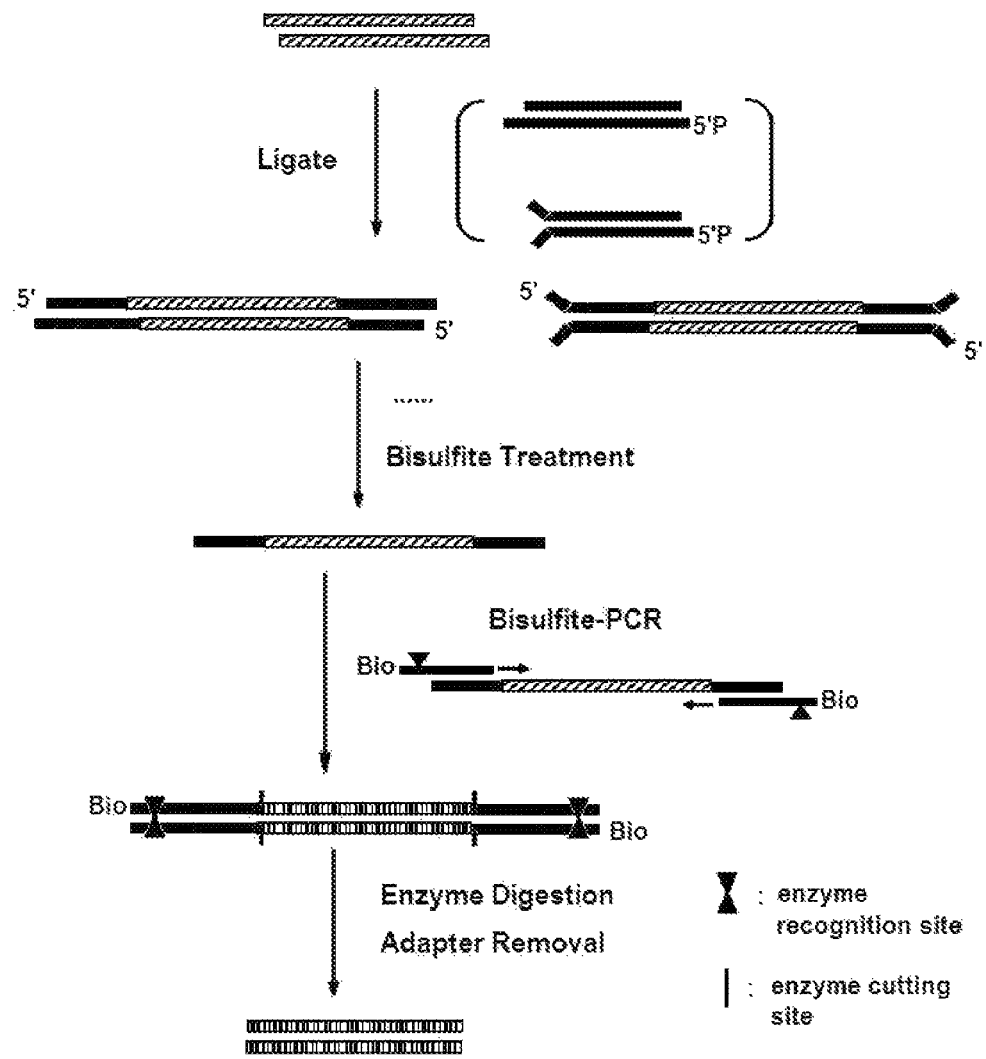

FIG. 6 shows linkage and removal manner (1) of an auxiliary adapter with a sticky end. The e) and g) auxiliary adapters may be used in this manner. A primer that matches with the sequence of auxiliary adapter after bisulfite treatment is designed, and meantime, a restriction enzyme recognition site is designed at the position close to the 5'-site of the primer.

Figure 7:
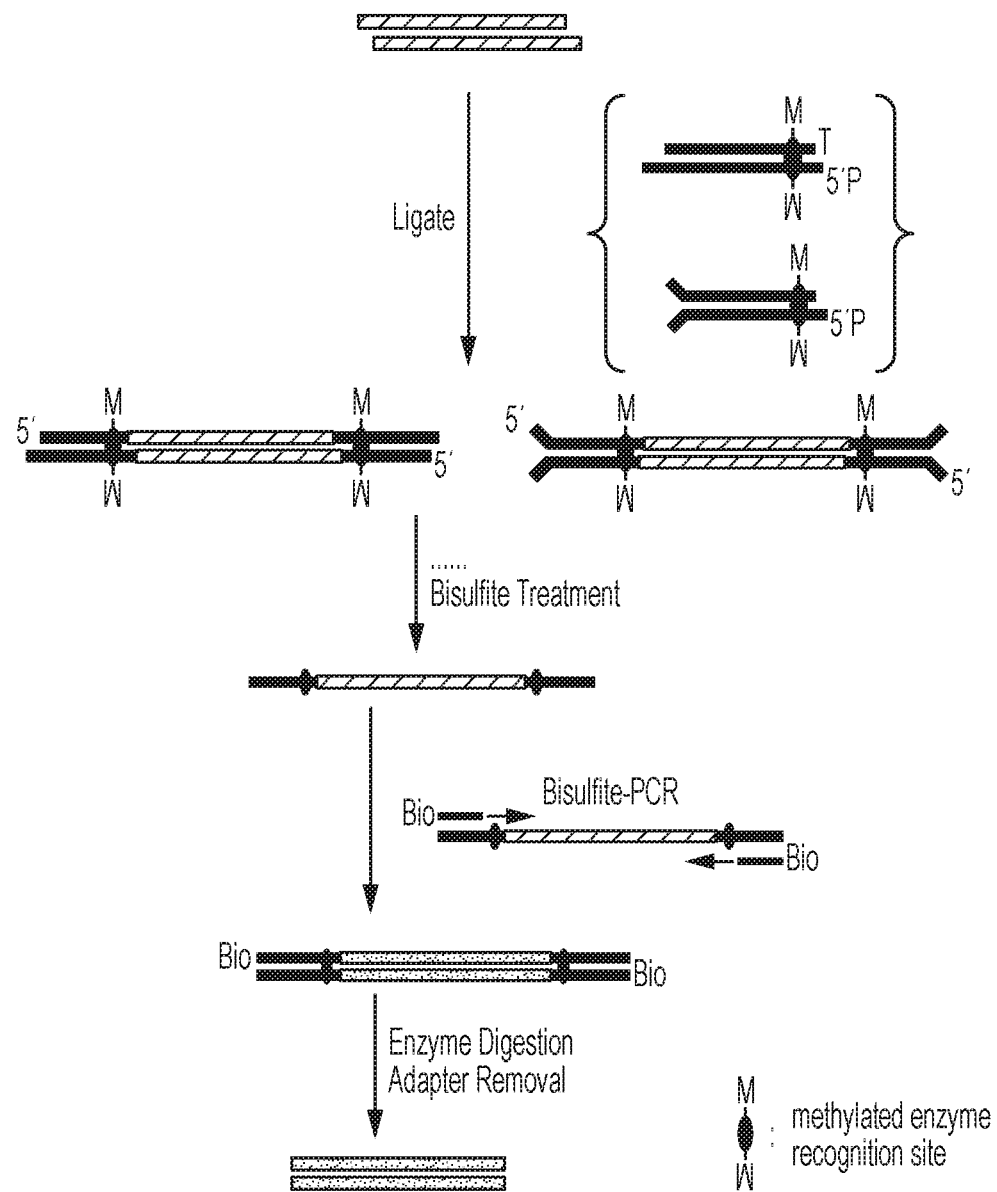

FIG. 7 shows linkage and removal manner (2) of an auxiliary adapter with a sticky end, i.e., the linkage and removal of the adapter, wherein the adapter comprises a methylated restriction enzyme cutting site. The f) and h) auxiliary adapters may be used in this manner. The auxiliary adapter comprises a methylated restriction enzyme cutting site to assure that the DNA fragments are not digested and the sequence of the restriction enzyme recognition is not changed after bisulfite treatment.

Figure 8:
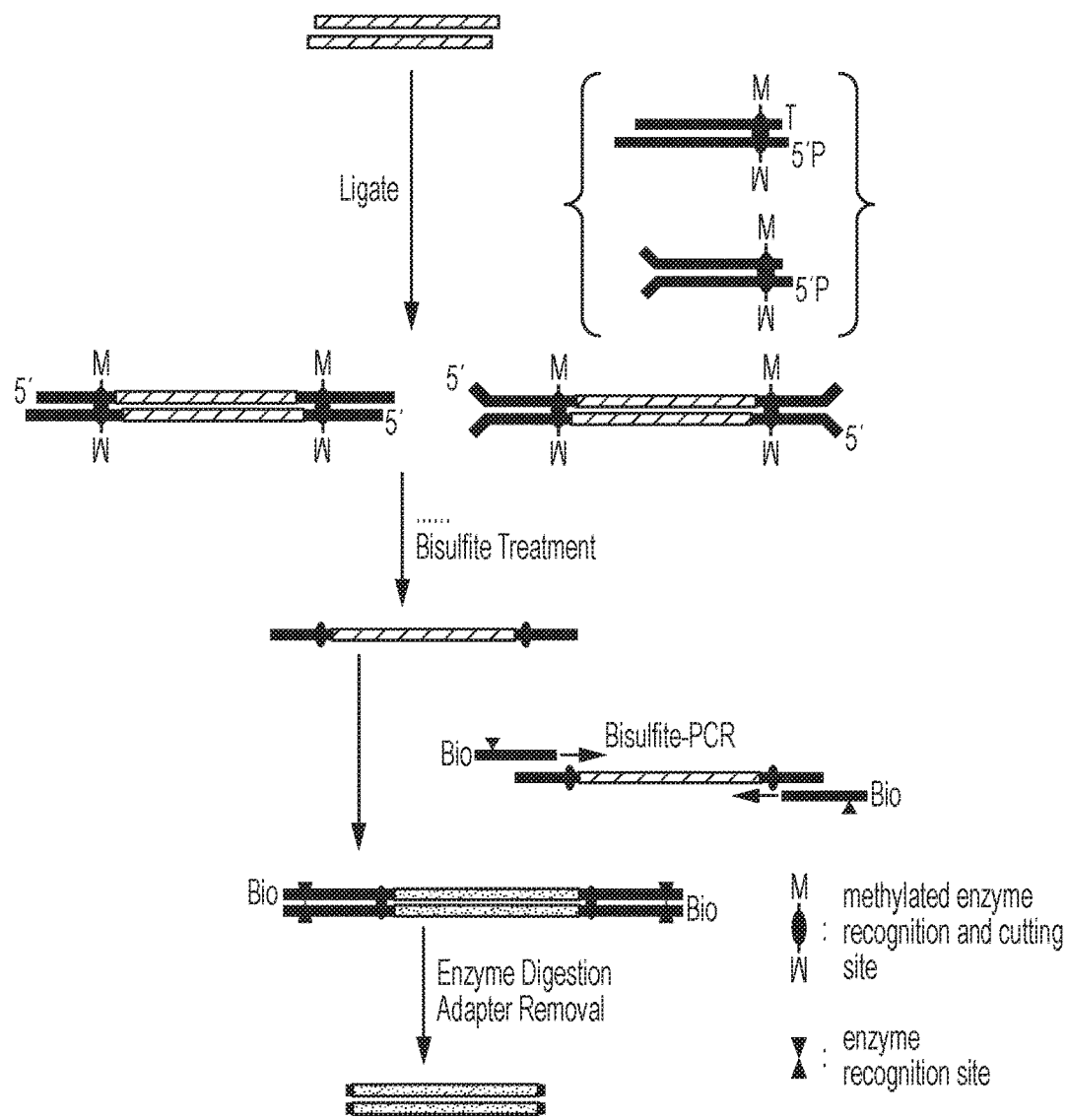

FIG. 8 shows linkage and removal manner (3) of an auxiliary adapter with a sticky end, i.e., the linkage and removal of the adapter, wherein the adapter comprises a methylated restriction enzyme cutting site and the primer comprises a restriction enzyme cutting site. A restriction enzyme cutting site is similarly designed close to the linkage site of the auxiliary adapter. Another restriction enzyme cutting site is designed at the 5'-end of the primer. The two restriction enzyme sites are overlapped by adjusting the length of the auxiliary adapter. The thoroughness of enzymatic digestion is assured by two enzymatic digestions.

Figure 9:
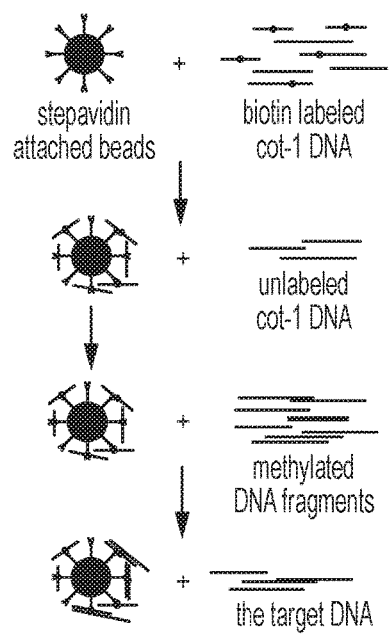

FIG. 9 is a schematic diagram of removal of methylated repetitive sequences. After C0T-1 DNA is labeled with biotin, the C0T-1 DNA labeled with biotin is bound to magnetic beads coated with avidin and the C0T-1 DNA fragments that are not labeled with biotin are removed by utilizing the principle that avidin-magnetic beads bind to biotin. The avidin-magnetic beads bound to the biotin-DNA are hybridized with methylated DNA fragments obtained by methylation immunoprecipitation, wherein the methylated repetitive sequences will be hybridized on the C0T-1 DNA labeled with biotin. The magnetic beads are separated and discarded. The DNA in the solution is recovered; and the recovered DNA is methylated DNA fragment in functional region.

Figure 10:
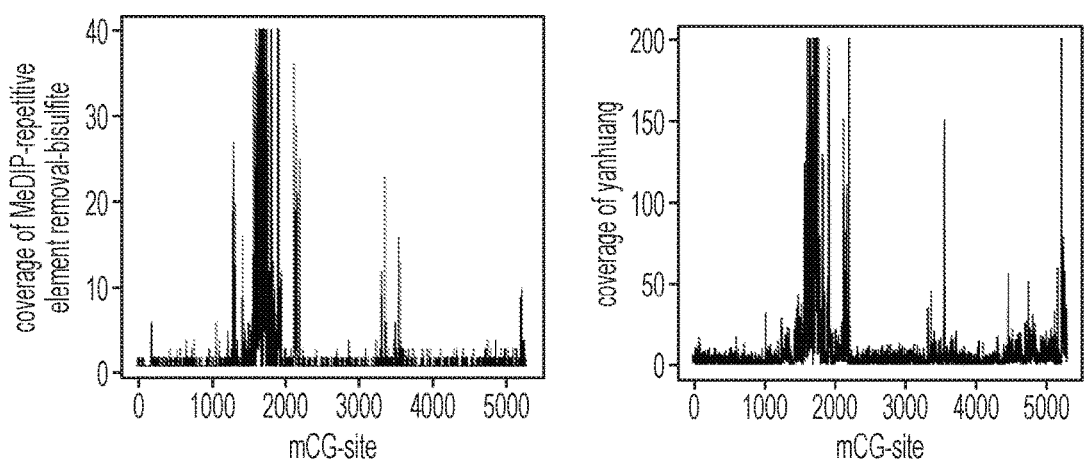

FIG. 10 shows sequencing depth analysis of an aligned single CPG site by comparing sequencing results of whole genome bisulfite treatment and sequencing results of the present technique. The comparison results show that the tendency of the sequencing depth of single CpG site is consistent. The left figure shows the sequencing results of MRERB, and the right figure shows the sequencing results of whole genome bisulfite treatment.

FIGS. 11-17 illustrate sequences of all type of auxiliary adapters and primers.

Figure 11:
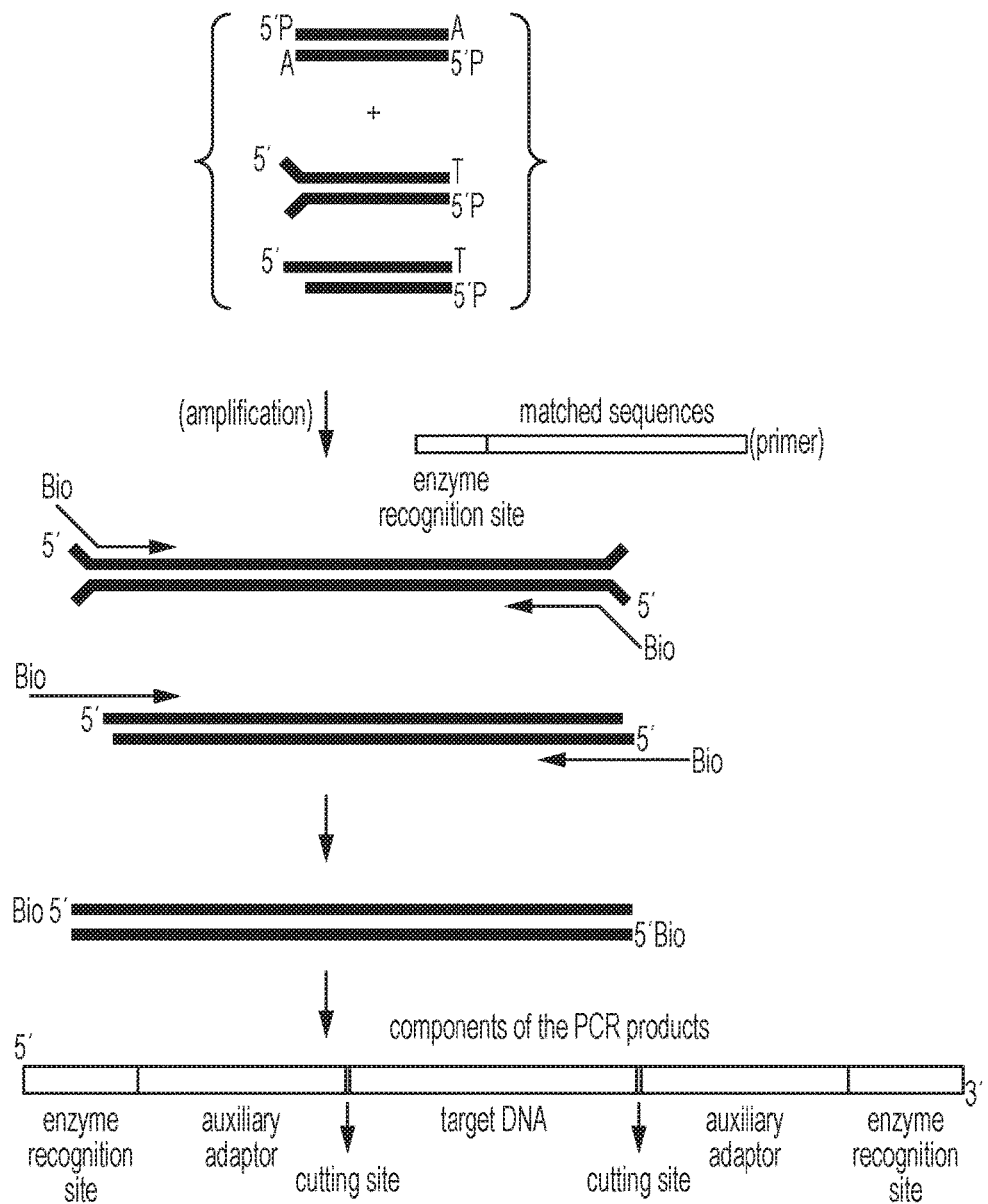

FIG. 11 shows adapter sequence and primer sequence in the linkage and removal manner (1) of an auxiliary adapter with a blunt end. The adapter sequence in the linkage and removal manner of auxiliary adapter does not comprise special base sequence, but it is required to assure that the adapter can be successfully amplified after bisulfite treatment. The joining-end of the adapter is designed to have overhanging "T" base at 3'-end and modified phosphate group at 5'-end so as to link to DNA in the form of "T-A" linkage. As for the removal of adapter from PCR product, a restriction enzyme recognition sequence is introduced to the 5'-end of the PCR primer. The enzyme is characterized in digesting DNA fragment at position of greater than 20 bp of downstream of the restriction enzyme recognition site and can remove the auxiliary adapter completely. In addition, a biotin group can be introduced to the 5'-end of the primer (the biotin group may not be introduced, and in this case, Ampure Beads may be used to remove small fragments). Therefore, the PCR product fragments before the removal of adapter include DNA fragment to be detected, two symmetrical restriction enzyme cutting sites, and symmetrical matched adapter sequence and its two symmetrical restriction enzyme recognition site sequences.

Figure 12:
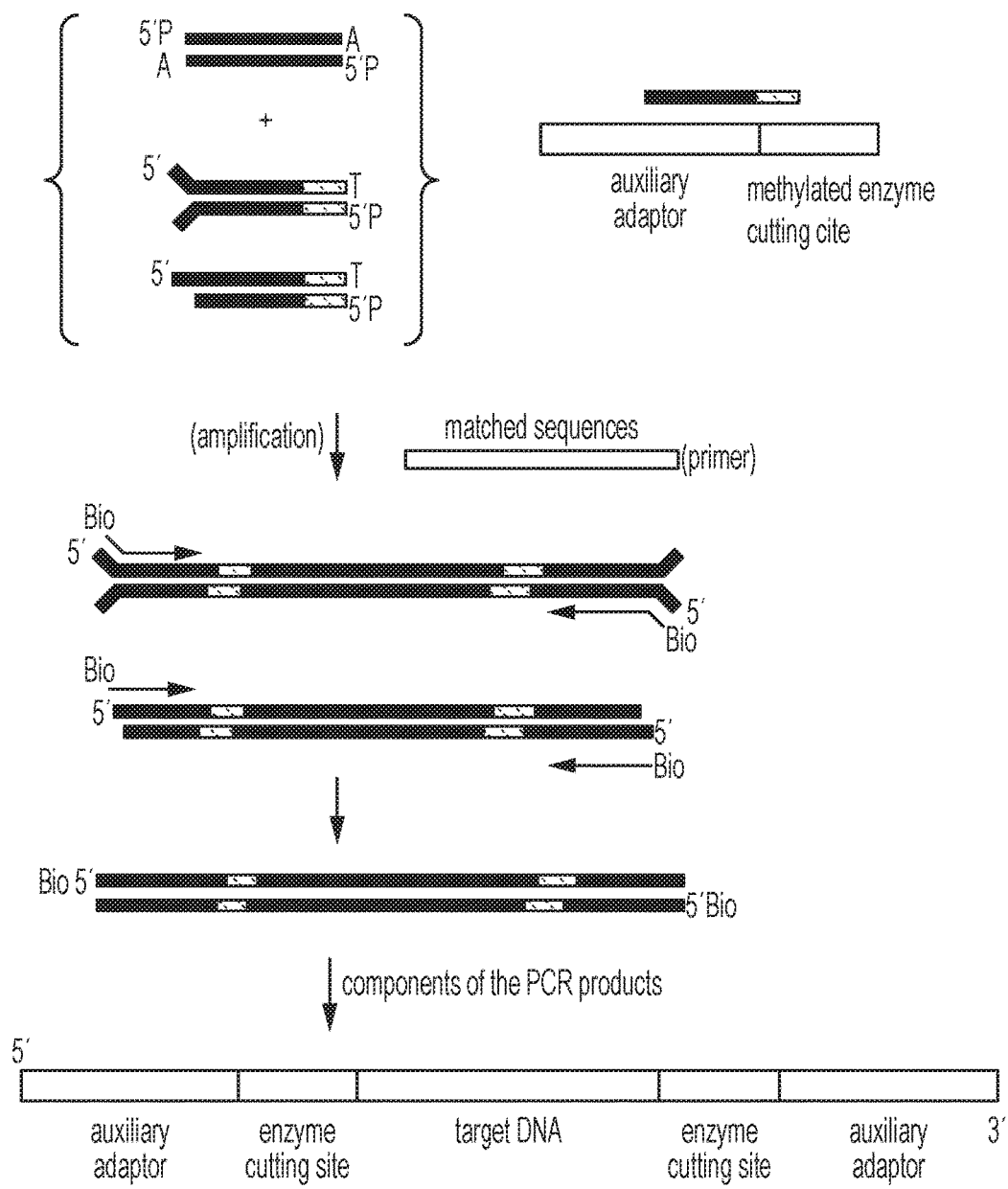

FIG. 12 shows adapter sequence and primer sequence in the linkage and removal manner (2) of an auxiliary adapter with a blunt end. The adapter sequence in the linkage and removal manner comprises a 20-30 bp sequence that can assure that the adapter can be successfully amplified after bisulfite treatment and a methylated restriction enzyme recognition sequence. The enzyme is characterized in that the enzyme recognition site and enzyme cutting site are the same. The joining-end of the adapter is designed to have overhanging "T" base at 3'-end and modified phosphate group at 5'-end so as to link to DNA in the form of "T-A" linkage. As for the removal of adapter from the PCR product, since methylation modification is carried out for the adapter, the sequence is not changed after bisulfate treatment, and the adapter can be removed by enzymatic digestion with the enzyme. In addition, a biotin group can be introduced to the 5'-end of the primer (the biotin group may not be introduced, and in this case, Ampure Beads may be used to remove small fragments). Therefore, the PCR product fragments before the removal of adapter include DNA fragment to be detected, two symmetrical restriction enzyme cutting sequences, and symmetrical matched adapter sequence.

Figure 13:
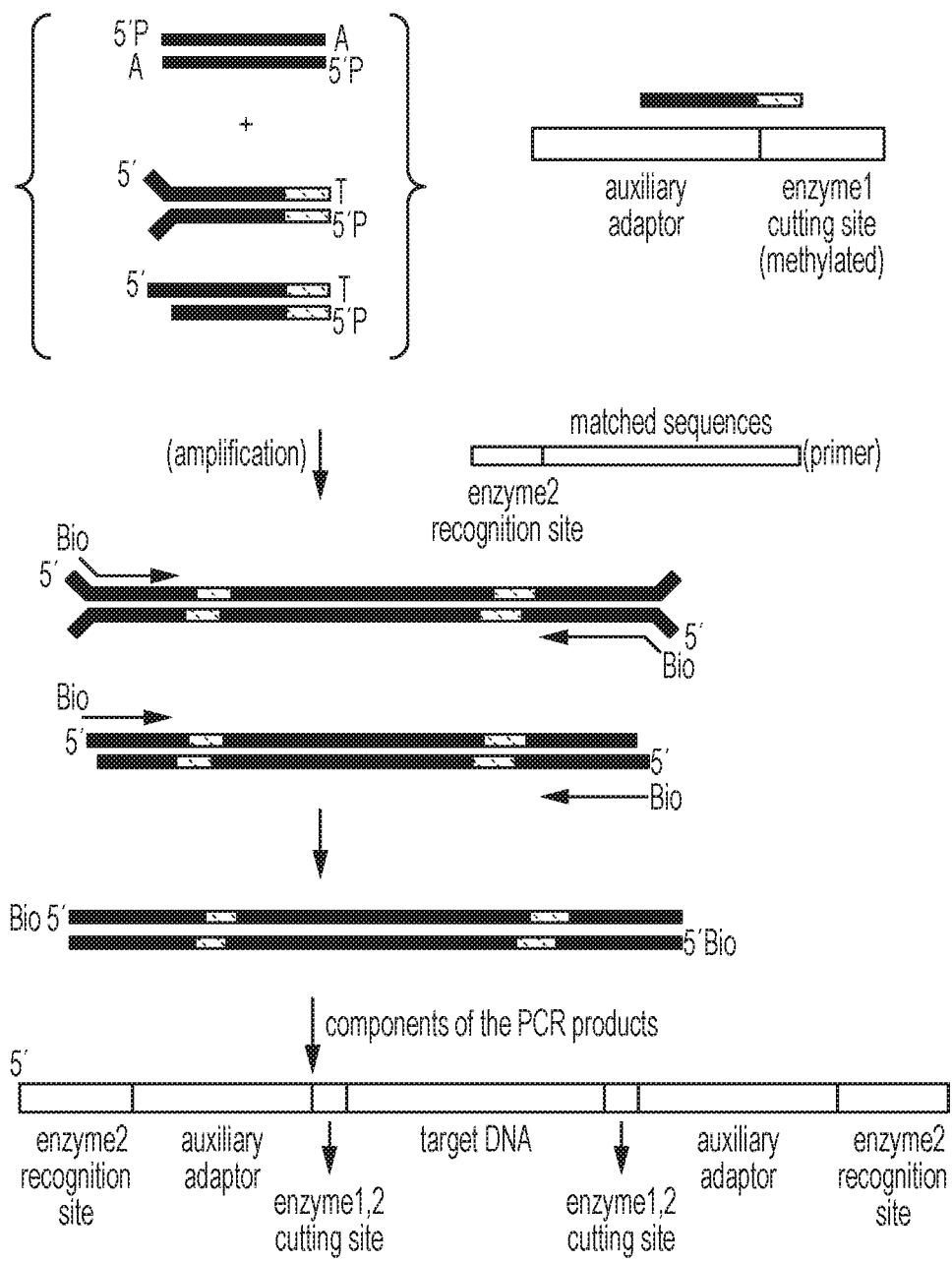

FIG. 13 shows adapter sequence and primer sequence in the linkage and removal manner (3) of an auxiliary adapter with a blunt end. The adapter sequence in the linkage and removal manner comprises a 20-30 bp sequence that can assure that the adapter can be successfully amplified after bisulfite treatment and a methylated restriction enzyme recognition sequence. The enzyme is characterized in that the enzyme recognition site and enzyme cutting size are the same. The joining-end of the adapter is designed to have overhanging "T" base at 3'-end and modified phosphate group at 5'-end so as to link to DNA in the form of "T-A" linkage. As for the removal of adapter from the PCR product, since methylation modification is carried out for the adapter, the sequence is not changed after bisulfite treatment, and the adapter can be removed by enzymatic digestion with the enzyme. Moreover, as for the removal of adapter from PCR product, a restriction enzyme recognition sequence is introduced to the 5'-end of the PCR primer. The enzyme is characterized in that it can digest DNA fragment at position of greater than 20 bp of downstream of the restriction enzyme recognition site and can remove the auxiliary adapter completely. In addition, a biotin group can be introduced to the 5'-end of the primer (the biotin group may not be introduced, and in this case, Ampure Beads may be used to remove small fragments). Therefore, the PCR product fragments before the removal of adapter include DNA fragment to be detected, two symmetrical restriction enzyme cutting sites for common digestion, and symmetrical matched adapter sequence and symmetrical two restriction enzyme recognition site sequences.

Figure 14:
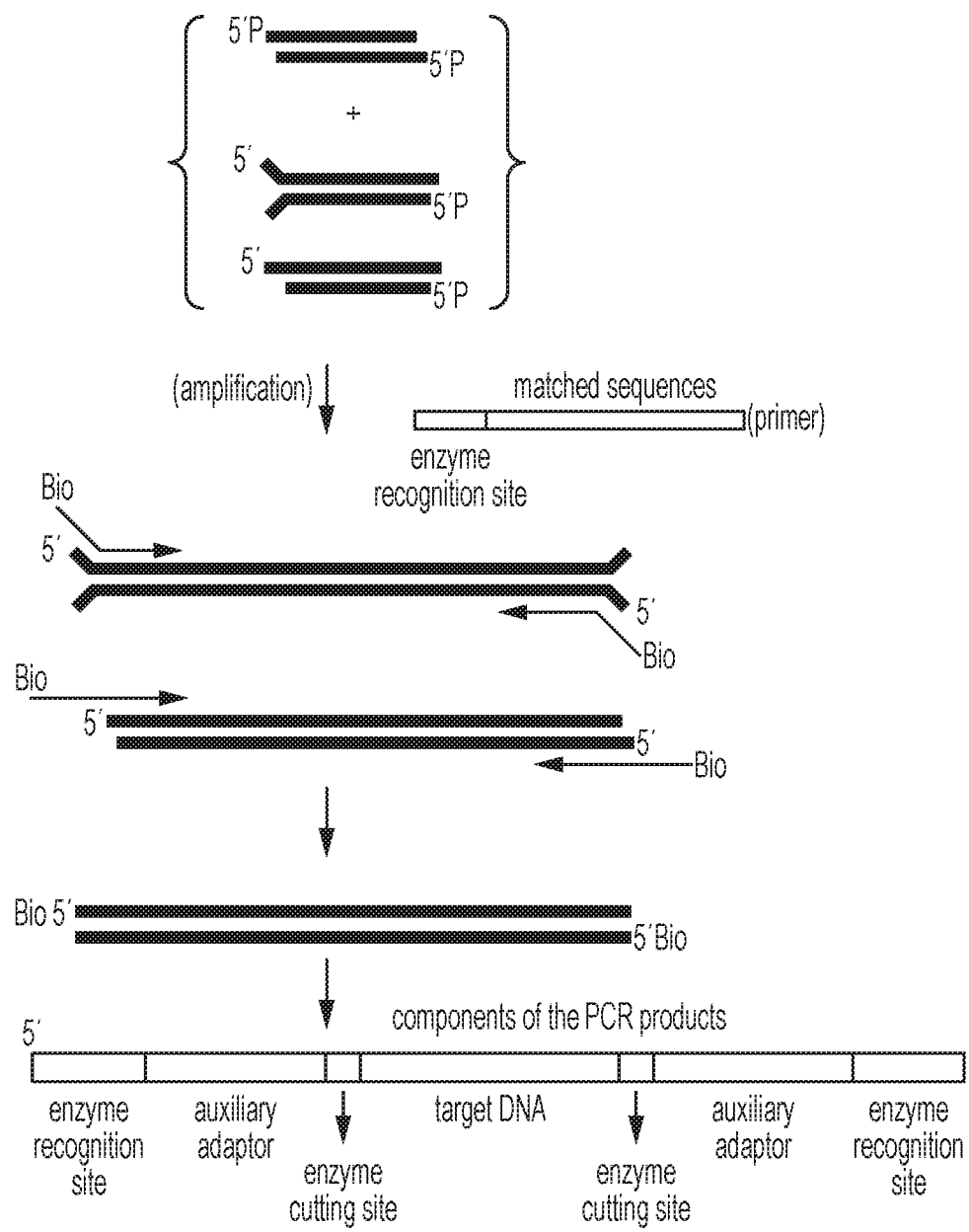

FIG. 14 shows adapter sequence and primer sequence in the linkage and removal manner (1) of an auxiliary adapter with a sticky end. The linkage and removal manners of the auxiliary adapter are the same as the linkage and removal manner (1) of an auxiliary adapter with a blunt end. The differences reside in that the 3'-end of the joining end of the adapter is linked in the form of non "T-A" linkage, and a sequence is designed to match with the sticky end sequence of the DNA.

Figure 15:
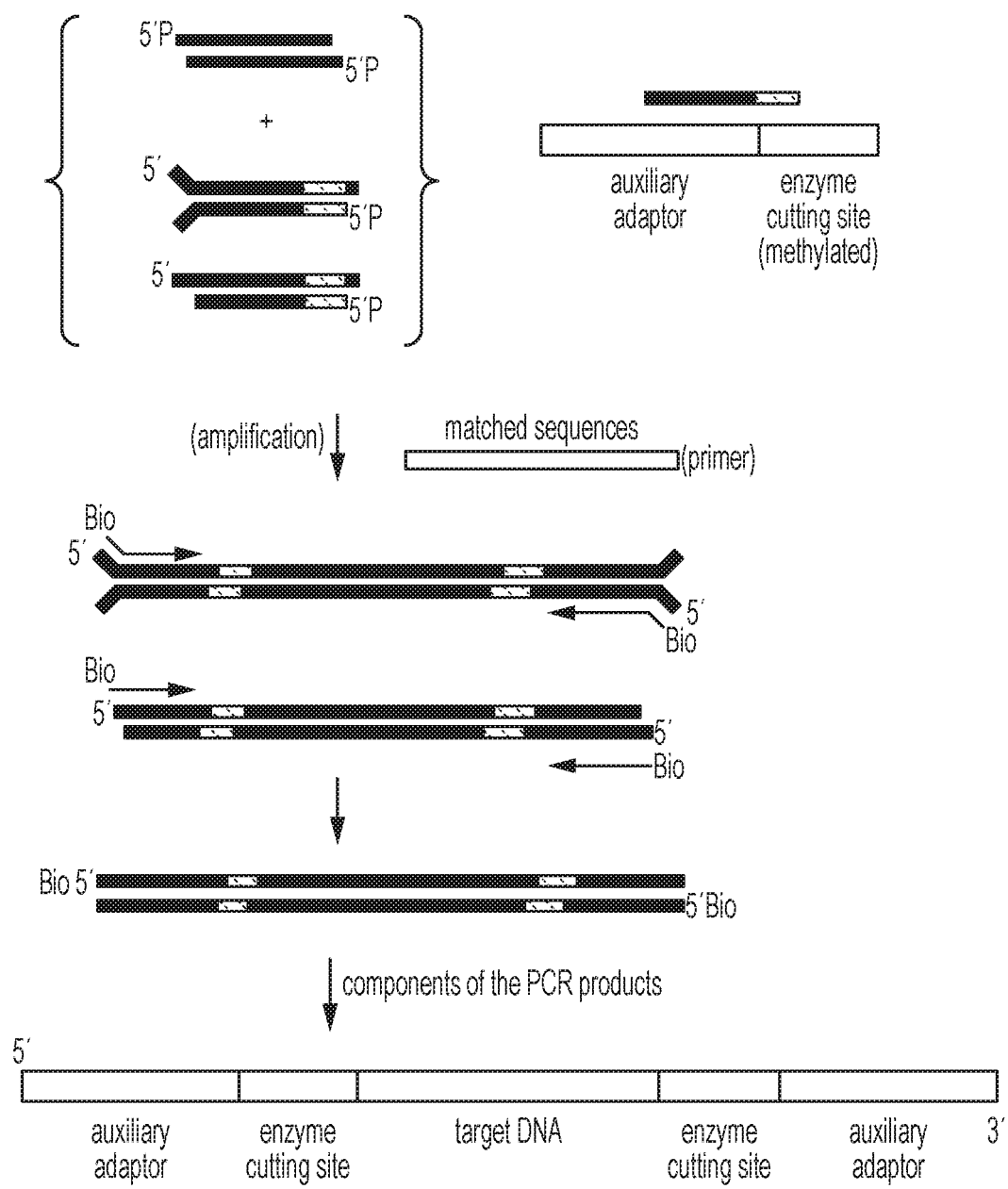

FIG. 15 shows adapter sequence and primer sequence in the linkage and removal manner (2) of an auxiliary adapter with a sticky end. The linkage and removal manners of the auxiliary adapter are the same as the linkage and removal manner (2) of an auxiliary adapter with a blunt end. The differences reside in that the 3'-end of the joining end of the adapter is linked in the form of non "T-A" linkage, and a sequence is designed to match with the sticky end sequence of the DNA.

Figure 16:
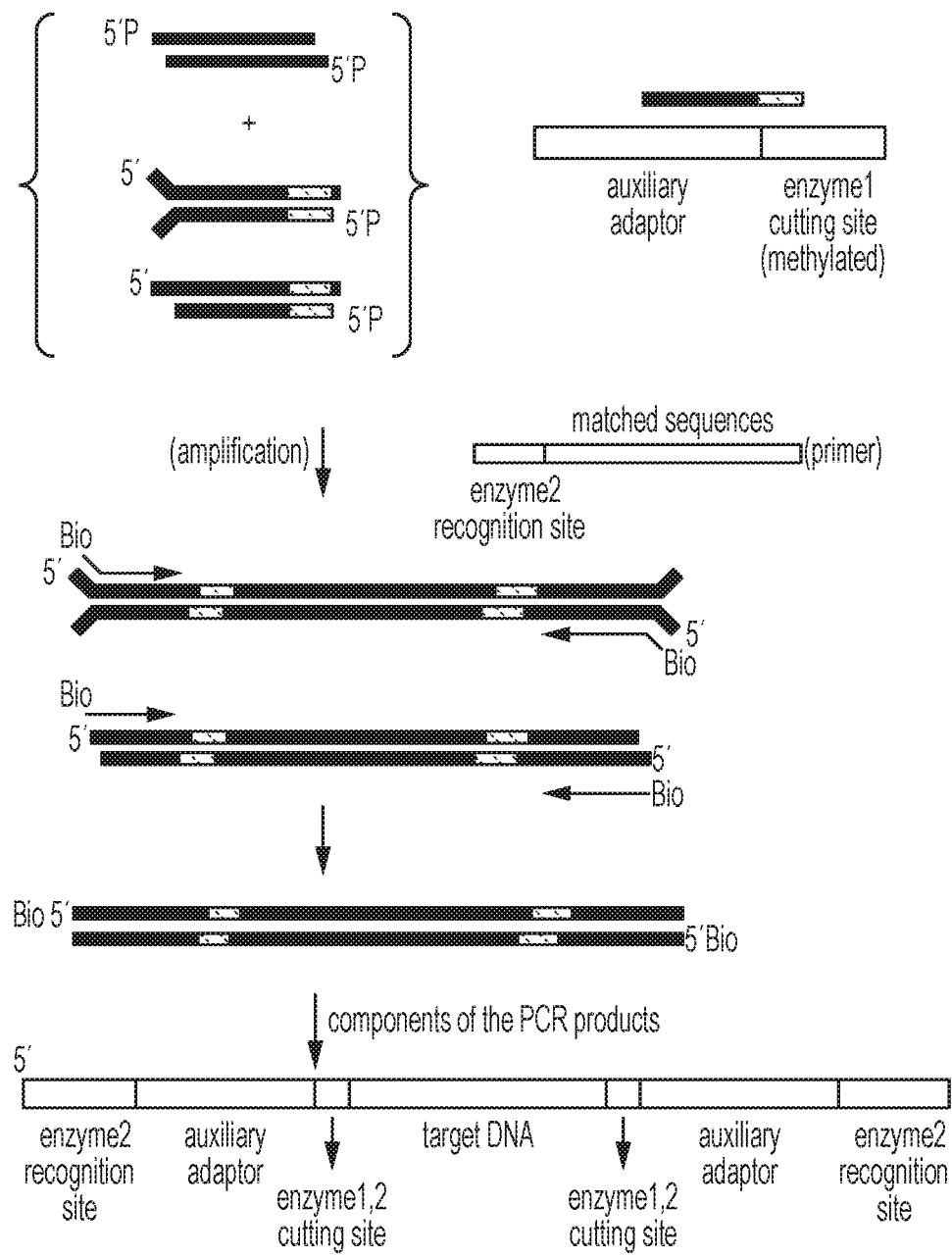

FIG. 16 shows adapter sequence and primer sequence in the linkage and removal manner (3) of an auxiliary adapter with a sticky end. The linkage and removal manners of the auxiliary adapter are the same as the linkage and removal manner (3) of an auxiliary adapter with a blunt end. The differences reside in that the 3'-end of the joining end of the adapter is linked in the form of non "T-A" linkage, and a sequence is designed to match with the sticky end sequence of the DNA.

Figure 17:
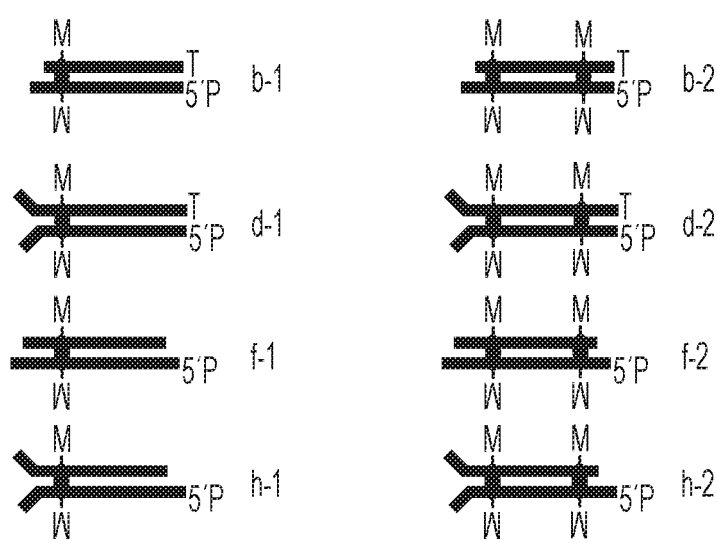

FIG. 17 illustrates design solution of other adapters.

The design solution of series 1 (b-1, d-1, f-1 and h-1) of auxiliary adapters is similar to the design solution of the b and d adapters, i.e., a restriction enzyme cutting site is designed on the position within 20-30 bp of upstream close to the linkage site of target DNA to the auxiliary adapter, and the restriction enzyme cutting site should have the following four characteristics: (1) the restriction enzyme cutting site comprises at least one methylated cytosine; (2) the restriction enzyme cutting site does not comprise unmethylated cytosine; (3) the restriction enzyme cutting site does not comprises CpG dinucleotide site; and (4) the restriction enzyme cutting site is designed on the position within 5 bp of upstream or downstream close to the linking site of DNA to be detected to the auxiliary adapter. The restriction endonuclease is selected from EcoP15I, Mme1, and the like. The primer is designed as a sequence complementary to the sequence of auxiliary adapter after E) conversion, and a single enzymatic digestion is performed by using the enzyme correspond to the designed methylated restriction enzyme cutting site when the step G) is carried out.

The design solution of series 2 (b-2, d-2, f-2 and h-2) of auxiliary adapters is a combination of the solution of series 1 of auxiliary adapters and the solution of b, d, f and h, that is, the two restriction enzyme cutting sites are overlapped by adjusting the length of the auxiliary adapter. The auxiliary adapter is removed by means of double enzymatic digestion. The primer is designed as a sequence complementary to the sequence of auxiliary adapter after E) conversion, and a double enzymatic digestion is performed by using an enzymes correspond to the designed restriction enzyme cutting sites when the step G) is carried out.

DETAILED DESCRIPTION OF THE INVENTION

Definitions

In order to more clearly illustrate the present invention, each of definitions used in the present invention is explained as follows.

DNA Fragmentation and Repair

DNA fragmentation refers to that genomic DNA is cut into small DNA fragments (e.g., several hundred or several thousand of bases) by mechanical or enzymatic digestion method etc.

The repair of DNA fragments refers to that, as to the DNA fragments after digestion, especially DNA fragments obtained by mechanical method, there may be the following situations for the ends of the DNA fragment: the breakage positions at the ends of the same side of the double strands are not consistent, there is a damage at the 3'-end or 5'-end. The repair of DNA fragments aims at polishing these ends or repairing the fragments with damaged 3'- or 5'-end into a blunt end structure with a phosphate group linked at 5'-end or a hydroxyl group linked at 3'-end.

According to the requirements of high throughput sequencers for sequencing library (WO2008096146A1), a DNA fragment library with suitable length is needed to be prepared. First of all, DNA is fragmented into DNA fragments with length suitable for sequencing by a sequencer.

The desired effects of fragmentation are that the fragments for library construction are lying in the main band of the fragmented DNA Smear. For example, if a Paired end library with 100 bp inserted is to be prepared, the main band of the broken DNA Smear is at 100 bp; if the effect of fragmentation is unsatisfied, fragmentation needs to be carried out again. Other breakage systems may be used in the fragmentation step of samples, and concrete parameters can be adjusted according to the requirements of devices.

The methods for breaking DNA include enzymatic digestion and ultrasonic breakage.

The method of enzymatic digestion utilizes a single endonuclease or a combination of several endonucleases that do not comprise CpG site to digest DNA. The enzymatic digestion method might render that some DNA fragments have unsuitable length and are excluded from the library due to the fixed restriction enzyme cutting sites; while ultrasonic breakage of DNA is random breakage of DNA and thus has unfixed breakage sites. Theoretically, the whole genome can be contained in the sequencing library. In the present experimental method, fragmentation of genome is performed by either enzymatic digestion or ultrasonic breakage. However, ultrasonic breakage is used in the examples.

As to DNA fragments obtained by ultrasonic breakage, the DNA fragments need to be repaired by end repairing to have a blunt end. The repair aims at phosphorylating the damaged 5'-end and hydroxylating the damaged 3'-end of the double stranded DNA fragments. The "A" base is added to the 3'-end of the DNA fragments with a blunt end to form "TA" sticky end linkage when linked to an auxiliary adapter. As to the fragmented genomic DNA obtained by enzymatic digestion with a combination of several enzymes, since sequences of ends obtained by enzymatic digestion are different, it is first that the DNA fragments are modified to have a blunt end, and then the "A" base is added to the 3'-end of the DNA fragments with a blunt end to form "TA" sticky end linkage when linked to an auxiliary adapter. As for fragmented DNA obtained by enzymatic digestion with a single enzyme and the DNA fragments have a blunt end, the "A" base is added to the 3'-end of the DNA fragments to form "TA" sticky end linkage when linked to an auxiliary adapter; if the DNA fragments have a sticky end, the auxiliary adapter can be designed to have a linkage end that matches with the sticky end of the DNA fragments to carry out sticky end linkage.

Linkage and Removal of Auxiliary Adapter

"Auxiliary adapter" means: addition of an auxiliary adapter aims at, after DNA is subjected to MeDIP and bisulfite treatment, it is possible to allow single-stranded DNA to be converted into double-stranded DNA via PCR reaction, so as to prepare a normal library.

The type of auxiliary adapter: the auxiliary adapter is classified according to methods of DNA fragmentation and methods of bases modification. At present, the bisulfite sequencing of methylation utilizes a methylated adapter (WO2009024019A1). Since all cytosine sites of this adapter are methylated, after the DNA fragment is linked to the methylated sequencing adapter and subjected to bisulfite treatment, the sequence of the adapter does not change, and still matches with the sequencing primer after PCR.

However, the methylated adapter interferes with the binding of a methylated antibody to methylated fragments in MeDIP experiment. Therefore, the adapter is not suitable for bisulfite sequencing of methylation after MeDIP. If an unmethylated adapter is linked prior to the MeDIP, bisulfite treatment will result in change in the adapter sequence, and the changed sequence does not match with the sequencing primer. If an adapter is not added prior to bisulfite treatment, the double-stranded DNA changes into sing-stranded DNA after MeDIP and bisulfite treatment and the sequence alters, and the Paired End Adapter and Paired End primer used in the construction of a normal library (taking solexa sequencing library as an example) cannot be used in the present experimental method. Thus, the inventors solve the problem associated with change in sequence after MeDIP and bisulfite treatment by introducing an auxiliary adapter (FIGS. 2 and 17), wherein, without affecting MeDIP, DNA fragment library is successfully amplified after bisulfite treatment and subsequent construction of normal library can be carried out.

Linkage and Cleavage of Auxiliary Adapters

The use of an auxiliary adapter is to solve the problem that altered sequence of adapter caused by methylated DNA immunoprecipitation and bisulfite treatment does not match with sequencing primer. The auxiliary adapter needs to be removed by digestion after bisulfite PCR to lower sequencing cost.

The linkage and cleavage of auxiliary adapter can be divided into the following several situations.

1. Linkage and enzymatic cleavage manner 1 of auxiliary adapter for DNA fragments obtained by multiple enzymatic digestion or ultrasonic breakage—primer comprises a restriction enzyme cutting site (FIG. 3).

DNA fragments obtained by multiple enzymatic digestion or ultrasonic breakage need to be linked to auxiliary adapters after end repairing and addition of "A" base to the 3'-end. The a) and c) auxiliary adapters can be used in this manner. No further modification is needed to make to the auxiliary adapter, except that phosphate group is added to 5'-end to facilitate linking to 3'-hydroxyl of the DNA fragment.

After the DNA fragment linked to auxiliary adapter is subjected to a series of treatments such as MedIP etc., a primer that matches with the sequence of auxiliary adapter after bisulfite treatment is designed (FIG. 3A), meantime a restriction enzyme recognition site is designed on position close to the 5'-site of the primer (FIG. 3B), wherein the restriction enzyme recognition site does not match with the sequence of the auxiliary adapter and is located at the extension portion of the primer. The restriction endonuclease is characterized by digesting DNA at 20-30 bp of downstream of the restriction enzyme recognition site. It is designed that the restriction enzyme cutting site within 5 bp range of end of DNA fragment to which the adapter auxiliary is linked by controlling the length of the auxiliary adapter. The DNA fragment has additional restriction enzyme recognition sites at two termini of the DNA after PCR, and the DNA fragment is digested at the cutting site by recognizing the double-stranded sequence with the enzyme. Since the primer is labeled with biotin at 5'-end, the cleaved auxiliary adapter by the enzyme and the undigested DNA fragment with auxiliary adapter can be removed rapidly and thoroughly by binding to avidin coated beads. The enzymes used in the primer include EcoP15I and Mme1.

In one embodiment of the present invention, the auxiliary adapter is linked and removed by a manner wherein a primer comprising restriction enzyme cutting sites (FIG. 2). The a) and c) auxiliary adapters can be used in the manner. A primer (A) that matches with the sequence of the auxiliary adapter after bisulfite treatment is designed, and a restriction enzyme recognition site (B) is designed at the position close to the 5'-site of the primer simultaneously, wherein the restriction enzyme recognition site does not match with the sequence of the auxiliary adapter and is located at extension portion of the primer. The restriction endonuclease is characterized by digesting DNA at 20-30 bp of downstream of the restriction enzyme recognition site. It is designed that the restriction enzyme cutting site within 5 bp range of end of DNA fragment to which the adapter auxiliary is linked by controlling the length of the auxiliary adapter.

2. Linkage and enzymatic cleavage manner 2 of auxiliary adapter for DNA fragments obtained by multiple enzymatic digestion or ultrasonic breakage—auxiliary adapter comprises a methylated restriction enzyme cutting site (FIG. 3)

In this manner, DNA fragments obtained by multiple enzymatic digestion or ultrasonic fragmentation need to be linked to auxiliary adapters after end repairing and addition of "A" base to the 3'-end, and the b) and d) auxiliary adapters can be used (FIG. 2). A restriction enzyme cutting site is designed on the position close to the linkage end of the b) and d) auxiliary adapters, and the purpose of design of such site resides in removing the auxiliary adapter by enzymatic digestion at the site after PCR. Therefore, the restriction enzyme cutting site is designed on the position close to the linkage end of the auxiliary adapter. As unmethylated cytosine will be converted into uracil after bisulfite treatment, and be turn to thymine after PCR, when a restriction enzyme cutting site is designed, if restriction enzyme recognition sequence comprises cytosine, the cytosine herein needs to be methylated to assure that the restriction enzyme recognition sequence does not change after bisulfite treatment. Since the adenosine (A) and thymine (T) increase in the PCR product after bisulfite treatment, in order that the DNA fragment is not digested, the inventors, when a restriction enzyme cutting site is designed, selected a restriction enzyme recognition site comprising a C at non-CpG site, and this cytosine is not located on the last position of the restriction enzyme recognition sequence. The enzymes that can be used herein include: AluI, BclI, BfaI, BglII, BsrGI, BspHI, CviAII, FatI, HindIII, HpyCH4V, NlaIII, NsiI, PciI, ScaI, SpeI, XbaI, and the like. In addition, a phosphate group is added to 5'-end of the auxiliary adapter to facilitate linking to 3'-hydroxyl of the DNA fragment.

After the DNA fragment linked with auxiliary adapter subject to a series of treatments such as MedIP etc., a primer that matches with the sequence of auxiliary adapter after bisulfite treatment is designed and the 5'-end is modified with a biotin (FIG. 4). Since the 5'-end of primer is modified with biotin, and the cleaved auxiliary adapter by the enzyme and undigested DNA fragment can be removed rapidly and thoroughly by binding to the avidin coated beads.

In one embodiment of the present invention, the auxiliary adapter is linked and removed by the manner wherein the auxiliary adapter comprises a methylated restriction enzyme cutting sites (FIG. 4). The b) and d) auxiliary adapters in FIG. 4 can be used in the manner. The auxiliary adapter comprises a methylated restriction enzyme cutting site to assure that the DNA fragment is not digested and the restriction enzyme recognition sequence does not change after bisulfite treatment.

3. Linkage and enzymatic cleavage manner 3 of auxiliary adapter for DNA fragments obtained by multiple enzymatic digestion or ultrasonic breakage3—auxiliary adapter comprises a methylated restriction enzyme cutting site and primer comprise a restriction enzyme cutting site (FIG. 5).

The enzymatic digestion with a single enzyme is usually not thorough enough, and sometimes, it is necessary to use two or more enzymes for the enzyme digestion. In this manner, DNA fragments obtained by multiple enzymatic digestion or ultrasonic breakage are linked to auxiliary adapters after end repairing and addition of "A" base to the 3'-end, and the b) and d) auxiliary adapters are used, which is similar to the manner 2 (FIG. 2). Also, a methylated restriction enzyme cutting site is designed on the position close to the linkage site.

A primer that matches the sequence of auxiliary adapter after bisulfite treatment is designed, which is similar to the manner 1, wherein a restriction enzyme cutting site is designed on the position close to the 5-site of the primer (FIG. 5). The enzyme digests the DNA at 20-30 bp of downstream of the restriction enzyme recognition site. It is designed that two restriction enzyme cutting sites on the same position of the DNA fragment by controlling the length of the auxiliary adapter. The digestion is thorough after two enzymatic digestions. Since the primer is labeled with biotin at 5'-site, the auxiliary adapter moiety cleaved by the enzyme and the undigested DNA fragment can bind to avidin and can be removed rapidly and thoroughly.

In one embodiment of the present invention, the auxiliary adapter is linked and removed by the manner wherein the auxiliary adapter comprises a methylated restriction enzyme cutting site and the primer comprises a restriction enzyme cutting site (FIG. 5). A methylated restriction enzyme cutting site is similarly designed on the position close to the linkage site of the auxiliary adapter. Another restriction enzyme recognition site is designed at the position close to the 5'-site of the primer. The two restriction enzyme recognition sites are overlapped by adjusting the length of the auxiliary adapter. The digestion is thorough after two enzymatic digestions.

4. Linkage and enzymatic cleavage manner 1 of auxiliary adapter for DNA fragments obtained by single enzymatic digestion—primer comprises a restriction enzyme cutting site (FIG. 6)

For the DNA fragments with a sticky end obtained by single enzymatic digestion, end repairing and addition of "A" base to the 3'-end are not necessary, and an auxiliary adapter that matches the sticky end can be directly designed. The e) and g) auxiliary adapters can be used in this manner. No further modification is needed to make to the auxiliary adapter except phosphorylation of its 5'-end to facilitate linking to 3'-hydroxyl of the DNA fragment.

After the DNA fragment linked to auxiliary adapter is subjected to a series of treatments such as MedIP etc., a primer that matches with the sequence of auxiliary adapter after bisulfite treatment is designed (FIG. 6), meantime a restriction enzyme recognition site is designed on position close to the 5'-site of the primer (FIG. 6), wherein the restriction enzyme recognition site does not match the sequence of the auxiliary adapter and is located at the extension portion of the primer. The restriction endonuclease is characterized by digesting DNA at 20-30 bp of downstream of the restriction enzyme recognition site. It is designed that the restriction enzyme cutting site within 5 bp range of end of DNA fragment to which the adapter auxiliary is linked by controlling the length of the auxiliary adapter. The DNA fragment has additional restriction enzyme recognition sites at two termini of the DNA after PCR, and the DNA fragment is digested at the cutting sites by recognizing the double-stranded sequence by the enzyme. Since the primer is labeled with biotin at 5'-end, and the cleaved auxiliary adapter moiety by the enzyme and undigested DNA fragment can be removed rapidly and thoroughly by binding to the avidin coated beads. The enzymes used in the primer include EcoP15I and Mme1.

In one embodiment of the present invention, the auxiliary adapter with sticky end is linked and removed by the manner wherein a primer comprises restriction enzyme cutting sites (FIG. 6). The e) and g) auxiliary adapters can be used in this manner. A prime that matches with the sequence of the auxiliary adapter after bisulfite treatment is designed, and a restriction enzyme recognition site is designed on the position close to the 5'-site of the primer simultaneously.

5. Linkage and enzymatic cleavage manner 2 of auxiliary adapter for DNA fragments obtained by single enzymatic digestion—auxiliary adapter comprises a methylated restriction enzyme cutting site (FIG. 7)

For the DNA fragments with a sticky end obtained by single enzymatic digestion, end repairing and addition of "A" base to the 3'-end are not necessary, and an auxiliary adapter that matches the sticky end can be directly designed. The e) and g) auxiliary adapters can be used in this manner. No further modification is needed to make to the auxiliary adapter except phosphorylation of 5'-end to facilitate linking to 3'-hydroxyl of the DNA fragments.

A methylated restriction enzyme cutting site is designed on the position close to the linkage end of the adapter. In order that the DNA fragment is not digested, when a restriction enzyme cutting site is designed, a restriction enzyme recognition site is selected to comprise a "C" at non-CpG site, and the cytosine is not located on the last position of the restriction enzyme recognition sequence. In order to assure that the restriction enzyme recognition sequence does not change after bisulfite treatment, the cytosine in the restriction enzyme recognition sequence is methylated while other bases are not modified. The enzymes that can be used herein include: AluI, BclI, BfaI, BglII, BsrGI, BspHI, CviAII, FatI, HindIII, HpyCH4V, NlaIII, NsiI, PciI, ScaI, SpeI, XbaI, and the like. In addition, a phosphate group is added to 5'-end of the auxiliary adapter to facilitate linking to 3'-hydroxyl of the DNA fragment.

After the DNA fragment linked to auxiliary adapter is subjected to a series of treatments such as MedIP etc., a primer that matches the sequence of auxiliary adapter after bisulfite treatment is designed and the 5'-end is modified with a biotin (FIG. 4). Since the 5'-end of primer is modified with biotin, and the cleaved auxiliary adapter moiety and undigested DNA fragment can be removed rapidly and thoroughly by binding to the avidin coated beads.

In one embodiment of the present invention, the auxiliary adapter is linked and removed by the manner wherein the auxiliary adapter comprises a methylated restriction enzyme cutting site (FIG. 7). The f) and h) auxiliary adapters can be used in this manner. The auxiliary adapter comprises a methylated restriction enzyme cutting site to assure that the DNA fragment is not digested and the restriction enzyme recognition sequence does not change after bisulfite treatment.

6. Linkage and enzymatic cleavage manner 3 of auxiliary adapter for DNA fragments obtained by single enzymatic digestion—auxiliary adapter comprises a methylated restriction enzyme cutting site and primer comprise a restriction enzyme cutting site (FIG. 8)

In one embodiment of the present invention, the enzymatic digestion with a single enzyme is usually not thorough enough, and sometimes, it is necessary that two or more enzymes are used to carry out the enzymatic digestion. In this manner, DNA fragments obtained by multiple enzymatic digestion or ultrasonic breakage are linked to auxiliary adapters after end repairing and addition of "A" base to the 3'-end, and the f) and h) auxiliary adapters, which is similar to the manner 2 (FIG. 8). Likewise, a methylated restriction enzyme cutting site is designed on the position close to the linkage site.

A primer that matches the sequence of auxiliary adapter after bisulfite treatment is designed, which is similar to manner 1, wherein a restriction enzyme cutting site is designed on the position close to the 5-site of the primer (FIG. 8). The enzyme digests the DNA at downstream 20-30 bp of the restriction enzyme recognition site. It is designed that the two restriction enzyme cutting sites on the same position of the DNA fragment by controlling the length of the auxiliary adapter. The digestion will be completely digested by two enzymes. Since the primer is labeled with biotin at 5'-site, and the digested auxiliary adapter moiety and undigested DNA fragment can be removed rapidly and thoroughly by binding to the avidin coated beads.

In one embodiment of the present invention, the auxiliary adapter is linked and removed by the manner wherein the auxiliary adapter comprises a methylated restriction enzyme cutting site and the primer comprises a restriction enzyme cutting site (FIG. 8). A methylated restriction enzyme cutting site is similarly designed on the position close to the linkage site of the auxiliary adapter. Another restriction enzyme recognition site is designed at the position close to the 5'-site of the primer. The two restriction enzyme recognition sites are overlapped by adjusting the length of the auxiliary adapter. The digestion is thorough after two enzymatic digestions.

Methylation Immunoprecipitation

Methylated DNA immunoprecipitation (MeDIP) consists in that 5-methylcytosine antibody can be used for immune-precipitating enriched methylated DNA fragments with high specificity. By combining the next generation sequencing technique, it is possible to carry out high-throughput screening of abnormally methylated gene. The method avoids limitation of enzyme cutting site when restriction enzymes are used. Methylated DNA immunoprecipitation technique used in the present invention is slightly modified from methylated DNA immunoprecipitation technique of Michael Weber, wherein the length of the DNA fragments is changed from 200-1000 bp to 100-300 bp to meet the requirement of the length of DNA fragments to be sequenced. In addition, the incubation time of the 5-methylcytosine antibody is optimized as 12 hours rather than 2 hours as reported in the reference.

Bisulfite Treatment

Bisulfite treatment refers to the chemical modification of single-stranded DNA molecules by using bisulfite, which results in removal of amino from unmethylated cytosine (C) by bisulfite to give uracil (U) whilst 5 mC cannot be modified and still retains as 5 mC. During PCR reaction, the uracil pairs with adenosine, and the uracil is replaced by thymine (T). This chemical reaction process was firstly reported by Frommer et al (M. Frommer et al, A genomic sequencing protocol that yields a positive display of 5-methylcytosine residues in individual DNA strands. Proc Natl Acad Sci USA 89 (1992) 1827-31), which comprises the following steps: the first step, sulfonation of cytosine by sodium bisulfite; the second step, deamination by hydroquinone; and the third step: disappearance of sulfo-group under basic environment to give uracil. At present, the experiment can be carried out by a Zymo bisulfite-Golden kit.

Digestion and Removal of Auxiliary Adapter

An enzyme is selected according to the design of auxiliary adapters, and a suitable amount of enzyme is utilized and enzymatic digestion time is prolonged to cleave the auxiliary adapter as thorough as possible. Considering the fact that enzymatic digestion is not thorough and short auxiliary adapter is difficult to be completely removed by using a normal kit, the inventor made biotin modification to the 5'-end of the primer, and used a method of binding magnetic beads coated with avidin to biotin to remove short auxiliary adapter and undigested DNA fragments.

DNA End Repairing and Linkage of Sequencing Adapter

The end of the DNA fragments digested by endonucleases is firstly repaired to match sequencing adapters (Solexa, 454, Solid). Taking Solexa as an example, if the end of digested DNA fragment is a sticky end, the end is firstly repaired into a blunt end, then "A" base is added to the 3'-end of the blunt end of the DNA. And a "T-A" linkage is formed with the PE adapter provided by Solexa. If the end of digested DNA fragment is a blunt end, "A" base is directly added to the 3'-end of the blunt end of the DNA, and then a "T-A" linkage is formed with the PE adapter provided by Solexa.

PCR

After DNA is subjected to bisulfite treatment, bisulfite-PCR aims at converting single-stranded DNA fragments into double strands to facilitate the linkage of a sequencing adapter and amplify DNA. The primer used in bisulfite-PCR matches the sequence of the auxiliary adapter after bisulfite treatment.

PE PCR: after the auxiliary adapter is removed by enzymatic digestion, PE adapter is added, and amplification is performed. The amplification aims at converting the forked PE adapter at the two termini of the DNA fragment into sequences that can match with the sequencing primer.

Sequencing

The DNA fragments from which auxiliary adapter is removed can be directly used in the conventional test steps of subsequent high throughput sequencing by Genome Sequencer FLX system, for example, GS FLX Standard DNA library of Roche Inc. is used to prepare a kit, or used in the conventional test steps of high throughput sequencing by Genome Analyzer (GA) system of Illumina Inc., for example, the Paired End DNA library is used to prepare a kit and to construct a conventional Paired End DNA sequencing library, or used in the conventional test steps of high throughput sequencing by SOLiD Library Oligos kit of Solid system of AB Inc.

EXAMPLES

The following examples illustrate the embodiments, and the embodiments are only used to explain and illustrate the invention, but are not to be taken as limiting the protection scope of the present invention. The equivalent variants envisaged by a person skilled in the art according to the common knowledge in the art and teachings of the prior art shall all be included in the protection scope of the present invention.

Example 1

The adapters, qPCR primer and PCR amplification primer for DNA after bisulfate treatment in the Examples are synthetic sequences which are synthesized by Invitrogen; the C0T1 DNA is purchased from Invitrogen; SYBR and relevant reagents from AB company are used in qPCR detection; and EcoP15I is purchased from NEB. The operational principle of the example is shown in FIG. 5.

Figure 1:
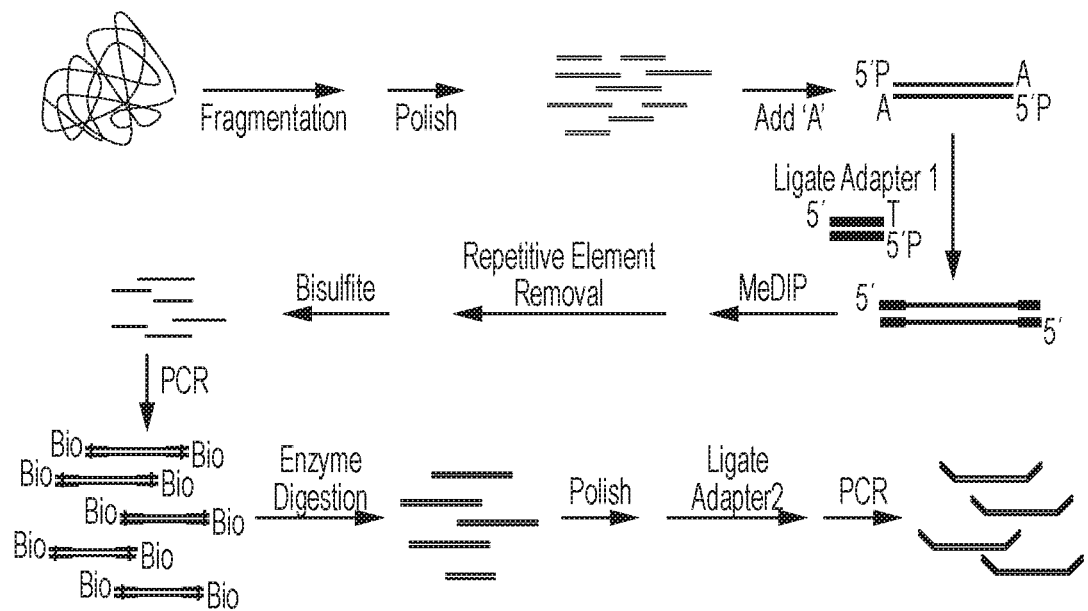
FIG. 1 is a schematic diagram of preparation of sequencing sample for methylated DNA in functional regions. The main experimental steps are orderly as follows: fragmentation of genomic DNA, end repairing of DNA fragments, addition of A base to 3'-end of the DNA fragments, linkage of an auxiliary adapter, methylation immunoprecipitation, removal of repetitive sequences from the methylated DNA fragments, bisulfite treatment of DNA, PCR amplification of the converted DNA using a primer designed according to the auxiliary adapter to obtain a double-stranded DNA, removal of the auxiliary adapter, end repairing of the PCR product from which the auxiliary adapter is removed and addition of A base to the 3'-end, linkage of a sequencing adapter, and sequencing.

1. Obtaining Genomic DNA 10 ml of blood sample (from volunteer) was drawn, and DNA was extracted from the sample by using QIAamp DNA Blood Mini Kit (Qiagen). The extracted DNA was numbered as YH-1. 10 µg of the DNA sample was used as starting material, and a library was constructed according to the process shown in FIG. 1. What was constructed in this example was Illumina GA System Paired End library.

2. Fragmentation of Genomic DNA

The DNA sample in the step 1 was fragmented by Covaris system (AB company). After the finishing of the fragmentation of sample, about 1/30 (volume ratio) of total fragmented sample was subjected to 1×TAE electrophoresis on 2% agarose gel, and DNA fragments to be detected were recovered from the electrophoresis gel. The sample DNA fragments were kept in the range of 100-500 bp by performing the following Covaris system fragmentation protocols:

1) Double clicking to run the Covaris main program "SonoLAB S-Series V2.54", then clicking "Start [Enter]", waiting until gas was discharged for 30 minutes, and water temperature was decreased to about 10° C. it should be determined whether the power switch of the breaking device and the cooling device was turned on before running the main program, or else the main program will display error message and it needs to try again.

2) adding 5 ng of the sample to a 100 µl of Covaris micro Tube and topping up to final volume of 100 µl with TE. The sample solution was well mixed by a pipette. Clicking "Configure", and setting the following parameters:

| Treatment 1 | Duty/cycle (%) | 10 |
|---|---|---|
| | Intensity | 5 |
| | Cycle/burst | 200 |
| | Time (s) | 960 |
| Cycle | | 16 | selecting mode as "Frequency Sweeping"; clicking "Save" or "Save As . . . " after all parameters were set to save the program; clicking "Return to Main Panel" to return to main screen; placing the breaking tube into the Covaris equipment, selecting the saved program, and starting breakage; Turning off the power of the breaking device and the cooling device after the breakage was finished by the configured program; and then closing breakage main program and the computer;

3) drawing out the broken sample in step 2) from the glass tube and placing into a 1.5 ml EP tube; subjecting 3 µl of the sample to 1×TAE electrophoresis on 2% agarose gel, recovering with QIAquick PCR purified kit; and dissolving the product into 32 µl of elution buffer (EB).

3. End Repair

10× polynucleotide kinase buffer and 10 mM of dNTPs mix were taken out from a kit (i.e., kit for constructing Illumina Paired End sequencing library) preserved at −20° C. and thawed on ice, and the 10× polynucleotide kinase buffer was thoroughly mixed. 100 µL of end repairing reaction system was formulated in a 1.5 mL centrifuge tube by mixing the 30 µL of the recovered fragmented product obtained in step 2), 45 µL of ultrapure water, 10 µL of 10× polynucleotide kinase buffer (B904), 4 µL of dNTP solution set (diluted and mixed as 10 mM each), 5 µL of T4 DNA polymerase, 1 µL of Klenow Fragment, and 5 µL of T4 polynucleotide kinase. After incubation at 20° C. for 30 minutes, the DNA subjected to end repairing was recovered and purified with an QIAquick PCR purifying kit, and the product DNA was dissolved in 34 µL of EB.

4. Addition of a Base

10× blue buffer and 1 mM of dATP were taken out from a kit (i.e., kit for constructing Illumina Paired End sequencing library) preserved at −20° C., then thawed on ice, and thoroughly mixed. 50 µL of a reaction system for the addition of "A" to the DNA was formulated in a 1.5 mL centrifuge tube by mixing the 32 µL of the recovered purified end-repaired product obtained in step 3), 5 µL of 10× blue buffer, 10 μL of dATP (diluted to 1 mM, GE company), and 3 μL of Klenow (3'-5' exo-). After incubation at 37° C. for 30 minutes, the DNA to which "A" was added was recovered and purified with a QIAquick PCR purifying kit. The product was dissolved into 32 μL of EB. 1 μL of the product was measured by NanoDrop 1000 to measure OD values, and concentration of sample, OD260/280 ratio, and OD260/230 ratio etc. were recorded.

5. Linkage of Auxiliary Adapter 1

2× Rapid linkage buffer and Alu Linker were taken out from a kit (i.e., kit for constructing Illumina Paired End sequencing library) preserved at −20° C. and thawed on ice, and the 2× Rapid linkage buffer was thoroughly mixed. 100 μL of a linkage reaction system was formulated in a 1.5 mL centrifuge tube by mixing the 30 μL of recovered product to which "A" was added obtained in step 3), 50 μL of 2× Rapid linkage buffer, 6 μL of auxiliary adapter (50 μM) (5'-AGCTGGGCACCGCTCATGCCACTCCGGCT (SEQ ID NO:1), 5'-pGCCGGAGTGGCATGAGCGGTGCCCAG (SEQ ID NO:2)), 10 μL of T4 DNA ligase, and 4 μL of ultrapure water. After incubation at 20° C. for 15 minutes, the DNA to which the auxiliary adapter 1 was added was recovered and purified with ZYMO DNA Clean & ConcentratorPTMP-5 (ZYMO company), and the product was dissolved in 40 μL of TE.

(1) TE was added to the sample form the step 5 comprising about 4 μg of DNA (according to the measured results by NnaoDrop 1000 in step 4) to 450 μL, thoroughly mixed, treated in a water bath at a temperature of 98° C. for 10 minutes, and placed on ice for 10 minutes.

(2) 51 μL of 10×IP buffer and 100 μL of Anti-5-Methylcytosine Mouse mAb (Abcam company) were added to the sample, and thoroughly mixed. The sample was vertically placed on rotator, and incubated at 4° C. for 12 hours.

(3) 30 μL, of Dynabeads M-280 goat anti-mouse IgG (Invitrogen company) was taken out, and magnetic beads were washed with 80 μL of 0.1% PBS-BSA for twice, to which 30 μL of 1×IP buffer was added, and thoroughly mixed.

(4) Dynabeads were added to the DNA-Antibody mixture, and mixed by vibrating at 4° C. for 3 hours.

(5) The magnetic beads were washed with 800 μl of 1×IP buffer for three times, wherein the first washing was performed by vortex for 2-4 seconds and for three times, and the latter two washings were performed by repeated mixing with a pipettor. After collected with magnetic shelf, the supernatant was discarded.

(6) 200 μL of propeinase K digestion buffer and 3 μL of propeinase K (50 μg/μl) were added, and incubated in an oven at 50° C. for 3 hours.

(7) The DNA in the reaction system in step (6) was recovered with ZYMO DNA Clean & ConcentratorPTMP-5, wherein binding buffer was present in 7 times of the DNA solution (step 6), and dissolved into 20 μL of ultrapure water heated in a water bath of 60° C. 1 μL of the product was measured by NanoDrop 1000 to measure OD values, and concentration of sample was recorded. Effects of MeDIP were determined by Q-PCR detection.

7. Removal of Repetitive Sequences with C0T1 DNA (1) Labeling of repetitive sequences with biotin: 4 μL of C0T 1 DNA (100 ng/μL) (Invitrogen company), 8 μL of a random primer (8N, 1 ug/μL) (Invitrogen company) and 25 μL of ultrapure water were added to a 1.5 mL tube, incubated at 97° C. for 10 minutes, and placed on ice for 10 minutes. 5 μL of 10× Klenow buffer, 5 μL of biotin/dNTP mix (Biotin-16-dUTP: 0.35 mM; dTTP: 0.65 mM; dCTP: 1 mM; dGTP: 1 mM; dATP: 1 mM) and 3 μL of Klenow Enzyme (exo-, Fermentas) were added to the tube to make a final reaction volume of 50 μL. The reaction solution was incubated at 37° C. for overnight, and to which 1 μL of Klenow Enzyme was added in the next day, and the reaction was continued for 3-5 hours. After the reaction was finished, the DNA in the reaction system was recovered and purified with a QIAquick PCR purifying kit. The product was dissolved into 100 μL of EB. Nano-drop1000 was used to determine the concentration. If the total mass was less than 2 μg, it may be recognized that the label was unsuccessful, and label was required to be carried out again.

(2) 100 μL of Streptavidin-Dynabeads® M-280 (Invitrogen) was added to a 1.5 mL of non-sticky tube, and magnetic beads were washed twice with 800 μL of TE buffer or 1× B&W buffer (5 mM Tris-HCL pH 7.5, 0.5 mM EDTA, 1M NaCl).

(3) The magnetic beads were resuspended in 100 μL of 2× B&W buffer (10 mM Tris-HCL pH 7.5, 1 mM EDTA, 2M NaCl).

(4) The C0T-1 DNA labeled with biotin (pre-denatured, treated at 97° C. for 10 minutes, and placed on ice for 10 minutes) was added to the magnetic beads (step (3)).

(5) spin at room temperature and low speed for 1 hours; and (6) the supernatant was discarded, and the beads were gently washed twice with 1× B&W buffer.

(7) The DNA sample after MeDIP was pumped to dryness, to which 100 μL of preheated hybridization solution at 65° C. was added, fed to the non-sticky tube containing magnetic beads, and overturned at 65° C. for overnight.

(8) The supernatant over the magnetic beads was transferred to a new 1.5 ml Eppendorf tube, purified with ZYMO-5, wherein binding buffer was present in an amount of 7 times, and 22 μL was eluted. 1 μL of the product was measured by NanoDrop 1000 to measure OD values, and the concentration of the sample was recorded.

8. Bisulfite Treatment

ZYMO EZ DNA Methylation-Gold Kit PTMP (ZYMO company) was used to carry our bisulfate treatment.

(1) 130 μL of CT conversion agent was added to each 20 μL of DNA sample in a PCR tube. If the volume of the DNA sample is less than 20 μL water was used to top up. The sample was mixed by slightly tapping the tube or pipettor operation.

(2) The sample tube was placed in a thermal cycler and operation was performed according to the following steps: placing at 98° C. for 10 minutes and then at 64° C. for 2.5 hours, and after which, the following operations was carried out immediately or stored at 4° C. (for at most 20 hours).

(3) 600 μL of M binding buffer was fed to Zymo-Spin ICPTMP column, and the column was placed in a collecting tube provided by the kit.

(4) The sample (from the step 2) was packed into Zymo-Spin ICPTMP column comprising M binding buffer. Lid the column and was overturned for several times to mix the sample.

(5) centrifuge at full speed (>10,000×g) for 30 seconds to remove effluent.

(6) 200 μL of M washing buffer was fed to the column, and centrifuge at full speed for 30 seconds.

(7) 200 μL of M-Desulphonation was fed to the column and put at room temperature (20° C.-30° C.) for 15-20 minutes. After culture, centrifuge at full speed for 30 seconds.

(8) 200 μL of M washing buffer was fed to the column, and centrifuge at full speed for 30 seconds. 200 μL of M washing buffer was added, and for 30 seconds.

(9) 20 μL of M eluting buffer was fed to the matrix of the column, the column was placed in a 1.5 ml of tube, and the DNA was eluted by means of centrifuge at full speed.

9. Amplification of DNA after Bisulfite Sulfonation Treatment (1) JumpStartPTMP Taq DNA polymerase was taken out from a kit preserved at −20° C. and thawed on ice, and thoroughly mixed. 50 μL of PCR reaction system was formulated in a 0.2 mL PCR tube by mixing 5 μL of product purified after bisulfite treatment, 5 μL of 10×PCR buffer (Sigma), 4 μL of dNTP, 0.5 μL of JumpStartPTMP Taq DNA polymerase (Sigma), 2 μl of auxiliary adapter primer 1.0 (10 pmol/μL) (Invitrogen), 2 μL of auxiliary adapter primer (10 pmol/μL) (Biotin-5'-GGTCAGCAGCTAAACACCACT-CATACCACTCCA (SEQ ID NO:3), Biotin-5'-GGTCA-GCAGTTGGGTATTGTTTATGTTATTTTGGT (SEQ ID NO:4)) (Invitrogen), and 35.5 μL of ultrapure water.

(2) The following amplification procedure was carried out in a thermal cycler: 94° C. for 10 seconds, 10 cycles of 94° C. for 30 seconds/52° C. for 30 seconds/72° C. for 30 seconds, and 72° C. for 5 minutes, and storing at 4° C.

(3) After the reaction was finished, The DNA in the reaction system was recovered and purified with a QIAquick PCR purifying kit, and the product was dissolved in 50 μL of EB. 1 μL of the product was measured by NanoDrop 1000 to measure OD values, and the concentration of sample was recorded.

10. Removal of the Auxiliary Adapter 1 by Enzymatic Digestion (1) 100 μL of reaction system was formulated in a 1.5 mL centrifuge tube by mixing PCR amplification product (~350 ng, not excess 400 ng), 10 μL 10× buffer 3 (NEB), 1 μL of 100×BSA, 2 μL of sinefungine (10 mM), 20 μL of 10×ATP, and 3 μL of EcoP15I (10 U/μL), and adding ultrapure water to 100 μL;

(2) enzymatic digestion was carried out at 37° C. for overnight, and 1 μL of the enzyme was added on the next day to continue the enzymatic digestion for 2 hours. The product was purified with ZYMO-5 wherein binding buffer was present in an amount of 5 times, and 50 μL eluted;

(3) 50 μL of Streptavidin-DynabeadsP®PM-280 (Invitrogen) was fed to a 1.5 mL non-sticky tube, and the magnetic beads were washed twice with 800 μL of TE buffer or 1× B&W buffer;

(4) the magnetic beads were resuspended in 50 μL 2× B&W buffer, and 50 μL of the enzyme digested product (step 2) was added;

(5) spin at room temperature for 30 minutes (speed was not excess of 600 rpm);

(6) the supernatant over magnetic beads was transferred to a new 1.5 ml Eppendorf tube, and purified with Qiagen (Mini). 1 μL of the purified product was measured by NanoDrop 1000 to measure OD values, and the concentration of the sample was recorded.

11. Sequencing

The DNA fragments from which the auxiliary adapter 1 was removed in the step 10 were directly applied to the subsequent Genome Analyzer (GA) system of Illumina company, and then subjected to high throughput sequencing. As to the experimental steps used herein, please refer to the construction of normal Paired End DNA sequencing library by Paired End DNA library construction kit.

Evaluation and Analysis of Results in Example 1

1. Detection of Enriching Effect of MeDIP

The enriching effect of MeDIP in the present invention was compared with the enriching effect of a commercial MeDIP kit (Diagenode) (Table 1), wherein methylation enriching effect (4994) was 62.71%, which was greater than methylation enriching effect of Diagenode, and non-methylation enriching rate (8804) was 0.33%, which was less than non-methylation enriching rate of Diagenode.

Therefore, the recovery rate of the present MeDIP method is within the range of recovery rate of the commercial MeDIP kit (Diagenode), and the present MeDIP method has an enriched quantity higher than that of the commercial kit. Thus, it is believed that the present MeDIP method is comparable to the commercial kit, and the experimental results are credible.

TABLE 1

MeDIP enriching efficiency of YH-1 DNA sample

| primer | | Diagenode | YH-adapter-U |
|---|---|---|---|
| 4994 | Recovery rate (%) | 43.65 | 62.71 |
| 8804 | | 0.76 | 0.33 |

2. Detection of Effect of EcoP15I Enzymatic Digestion

The EcoP15I enzyme digested product clone was picked and sequenced by Sanger method. The detection results showed (Table 2) that the digestion efficiency of EcoP15I was up to 86%. The high digestion efficiency of the enzyme demonstrated that the linker could be highly effectively cleaved, with no interfering in the subsequent tests such as linkage of an adapter.

TABLE 2

EcoP15I enzymatic digestion efficiency detection

| clone | EcoP15I |
|---|---|
| enzymatic digestion | 24 |
| non-enzymatic digestion | 4 |
| total amount | 28 |
| digestion efficiency (%) | 86 |

3. Detection of Sequencing Library by Sanger Method

The sequencing library prepared by the sequencing library sample preparing technique of the present invention was subjected to clone treatment, and the sequencing detection within small range was carried out by Sanger method. The results of detecting library showed (Table 3) that 76% of reads could be aligned back to genomic region, and the methylation rate thereof was up to 87%; the bisulfate (sulfonation) conversion rate of non-methylated cytosine was 99%; and amplification repetition rate of fragment was zero.

TABLE 3 sequencing results by Sanger method of YH-1 genome DNA library, the library was processed by methylation immunoprecipitation, removal of repetitive sequences in combination with bisulfite treatment

| library | YH-1 |
|---|---|
| Sequencing number | 71 |
| Alignment number | 54 |
| Alignment ratio | 0.76 |
| Methylation ratio | 0.87 |
| Conversion rate | 0.99 |
| amplification repetition rate | 0 |
| GC base content | 27.81% |

Example 2

The principle of Example 2 was shown in FIG. 6, wherein all steps were same as those in Example 1 except for the following. The following steps 5, 9 and 10 were used in place of the steps 5, 9 and 10 in Example 1, respectively.

5. Linkage of Auxiliary Adapter

2× Rapid linkage buffer and Alu Linker were taken out from a kit preserved at −20° C. and thawed on ice, and the 2× Rapid linkage buffer was thoroughly mixed. 100 µL of a linkage reaction system was formulated in a 1.5 mL centrifuge tube by mixing the 30 µL of recovered product to which "A" was added, 50 µL of 2× Rapid linkage buffer, 6 µL of auxiliary adapter (50 µM) (5'-CTGGGCACCGCTCATGCCACTCCGGCTAAG$^{5m}$CT (SEQ ID NO:5), 5'-pG$^{5m}$CTTAGCCGGAGTGGCATGAGCGGTGCCCAG (SEQ ID NO:6)), 10 µL of T4 DNA ligase, and 4 µL of ultrapure water. After incubation at 20° C. for 15 minutes, the DNA to which the auxiliary adapter was added was recovered and purified with ZYMO DNA Clean & ConcentratorPTMP-5 (ZYMO company), and the product was dissolved in 40 µL of TE.

(1) JumpStartPTNIP Taq DNA polymerase was taken out from a kit preserved at −20° C. and thawed on ice, and thoroughly mixed. 50 µL of PCR reaction system was formulated in a 0.2 mL PCR tube by mixing 5 µL of product purified after bisulfite treatment, 5 µL of 10×PCR buffer (Sigma), 4 µL of dNTP, 0.5 µL of JumpStartPTMP Taq DNA polymerase (Sigma), 2 µl of Alu I primer 1.0 (10 pmol/µL) (Invitrogen), 2 µL of auxiliary adapter primer (10 pmol/µL) (Biotin-5'-CTAAACACCACTCATACCACTCCA (SEQ ID NO:7), Biotin-5'-TTGGGTATTGTTTATGTTATTTTGGT (SEQ ID NO:8)) (Invitrogen), and 35.5 µL of ultrapure water.

(2) The following amplification procedure was carried out in a thermal cycler: 94° C. for 10 seconds, 10 cycles of 94° C. for 30 seconds/52° C. for 30 seconds/72° C. for 30 seconds, and 72° C. for 5 minutes, and storing at 4° C.

(3) After the reaction was finished, the DNA in the reaction system was recovered and purified with a QIAquick PCR purifying kit, and the product was dissolved in 50 µL of EB. 1 µL of the product was measured by NanoDrop 1000 to measure OD values, and the concentration of sample was recorded.

10. Removal of the Auxiliary Adapter by Enzymatic Digestion (1) 100 µL of reaction system was formulated in a 1.5 mL centrifuge tube by mixing PCR amplification product (<400 ng), 10 µL of 10× buffer 2 (NEB), and 3 µL of Alu I, and adding ultrapure water to 100 µL;

(2) enzymatic digestion was carried out at 37° C. for overnight, and 1 µL of the enzyme was added on the next day to continue the enzymatic digestion for 2 hours. The product was purified with ZYMO-5 wherein binding buffer was present in an amount of 5 time, and 50 µL elution;

(3) 100 µL of Streptavidin-DynabeadsP®PM-280 (Invitrogen) was transfer into a 1.5 mL non-sticky tube, and the magnetic beads were washed twice with 800 µL of TE buffer or 1× B&W buffer;

(4) the magnetic beads were resuspended in 50 µL 2× B&W buffer, and 50 µL of the enzyme digested product (2) was added;

(5) spin at room temperature for 30 minutes (speed was not excess of 600 rpm);

(6) the supernatant over magnetic beads was transferred to a new 1.5 ml Eppendorf tube, and purified with Qiagen (Mini). 1 µL of the purified product was measured by NanoDrop 1000 to measure OD values, and the concentration of the sample was recorded.

Evaluation and Analysis of Results in Example 2

1. Detection of Auxiliary Adapter Efficiency

Since the auxiliary adapter comprises a methylated cytosine, it was firstly detected whether or not this methylation site has influence on MeDIP. The auxiliary adapter was aligned, and an unmethylated adapter counterpart was designed. The amount of methylated or unmethylated auxiliary adapter was detected after MeDIP by using methylated detection primers numbered as 4994 and GAPDH or by using unmethylated detection primers numbered as 8804 and TSH2B, respectively. The detection results (Table 4) showed that the enriching rate of methylated auxiliary adapter was consistent with that of unmethylated auxiliary adapter. Therefore, the influence of methylated auxiliary adapter on background of MeDIP is neglectable.

TABLE 4

Validation of Influences of methylated and unmethylated auxiliary adapters on MeDIP

| primer | auxiliary adapter-U recovery rate (%) | auxiliary adapter-M recovery rate (%) |
|---|---|---|
| 4994 | 3.560 | 3.560 |
| 8804 | 0.023 | 0.028 |
| TSH2B | 0.014 | 0.015 |
| GAPDH | 13.810 | 11.390 |

2. Detection of MeDIP Enriching Effect

The MeDIP enriching effect was detected by using the primer (4994) for detecting methylation enriching effect and the primer (8804) for detecting non-methylation enriching effect, respectively (Table 5), wherein the methylation enriching efficiency was 45.6%, which was little different from the methylation enriching efficiency of Diagenode (Table 2); the non-methylation enriching efficiency was 2.9%, which was slightly higher than the non-methylation enriching efficiency of Diagenode but was far less than the methylation enriching efficiency. Therefore, the MeDIP enriching DNA effect was successful.

TABLE 5

MeDIP enriching efficiency of YH-1 DNA sample

| primer | | YH-adapter-M |
|---|---|---|
| 4994 | recovery rate (%) | 45.6 |
| 8804 | | 2.9 |

3. Detection of Alu I Enzymatic Digestion Effect

The Alu I enzyme digested product clones were picked and sequenced by Sanger method. The detection results showed (Table 6) that the two digestion efficiencies of Alu I were 94% and 100%. The digestion efficiency of the enzyme demonstrated that the linker could be highly effectively cleaved, with no interfering in the subsequent tests such as linkage of an adapter.

TABLE 6

Alu I enzymatic digestion efficiency detection

| clone | AluI (1st) | AluI (2nd) |
|---|---|---|
| Enzymatic digestion | 30 | 79 |
| Non-enzyme digfestion | 2 | 0 |
| Total amount | 32 | 79 |
| Digestion efficiency (%) | 94 | 100 |

4. Detection of Sequencing Library by Sanger Method

The sequencing library prepared by the sequencing library sample preparing technique of the present invention was subjected to clone treatment, and the sequencing detection within small range was carried out by Sanger method. The results of detecting library showed (Table 7) that 85% of reads could be aligned back to genomic region, and methylation rate was up to 93%, demonstrating that the DNA fragments linked to Alu I adapter can enrich sequences of most of methylated regions in the genome after MeDIP treatment. In addition, the high conversion rate of 97% indicated that the effect of bisulfite (sulfonation) treatment was very significant. Therefore, as to the DNA fragments linked to the Alu I adapter, after subjected to MeDIP treatment, removal of repetitive sequences, bisulfite treatment, and Alu I enzymatic digestion, the effective sequence information was still obtained. The library was qualified and used to construct Paired End DNA library for high throughput sequencing by GA system of Illumina company, and to carry out corresponding sequencing.

TABLE 7 sequencing results by Sanger method after YH-1 genome methylation immunoprecipitation, removal of repetitive sequences in combination with bisulfitetreatment of library

| library | YH-1 |
|---|---|
| Sequencing number | 75 |
| Alignment number | 64 |
| Alignment ratio | 0.85 |
| Methylation ratio | 0.93 |
| Conversion rate | 0.97 |
| amplification repetition rate | 0 |
| GC base content | 30.64% |

The inventors only exemplify the manners (1) and (2) for the linkage and removal of an auxiliary adapter with a blunt end in Examples 1 and 2, which possessed certain representation. Since manner (3) of the linkage and removal of an auxiliary adapter with a blunt end is a combined of the manners (1) and (2), the successful implementation of the manners (1) and (2) for the linkage and removal of an auxiliary adapter with a blunt end suggested that the manner (3) can be successfully carried out. As compared with an auxiliary adapter with a blunt end, the linkage manner of an auxiliary adapter with a sticky end was different in terms of manner of linkage of the adapter, and linkage efficiency of auxiliary adapter with a blunt end was lower than that of auxiliary adapter with a sticky end. Clearly, when the manners for the linkage and removal of an auxiliary adapter with a blunt end were successfully carried out, the manners (4)-(6) for the linkage and removal of an auxiliary adapter with a sticky end could also be successfully carried out.

5. Comparison with Effective Data Obtained by Bisulfite Sequencing Method

High throughput sequencing was carried out by GA system of Illumina company, wherein the sequencing was 45 cycle Paired End sequencing. The concrete sequencing procedure and reagents were standard procedure and kits of Illumina company. 2.53 Gb data were obtained by such sequencing, and half of them could be aligned (mapping) to reference genome (homo sapiens), which was similar to alignment ratio of other bisulfite sequencing [H. Xiang et al, Single base-resolution methylome of the silkworm reveals a sparse epigenomic map. Nat Biotechnol 28 516-20]. The concrete results were shown in Table 8, wherein the DNA average methylation level was up to 84.2%, which was higher than 70% methylation level in whole genome methylation sequencing, demonstrating that the MeDIP had a high specificity for binding methylated cytosine.

TABLE 8

Sequencing results by GA system of YH-1 genome DNA library, the library was obtained after methylation immunoprecipitation, removal of repetitive sequences in combination with bisulfite treatment

| library | YH-1 |
|---|---|
| total data | 57,510,098(2.53 Gb) |
| total data after filtration | 57,049,532 |
| filtration ratio | 0.80% |
| aligned number | 30,287,175 |
| alignment ratio | 53.09% |
| amplification repetition ratio | 5.83% |
| effective data | 28,619,720(1.27 Gb) |
| ratio of effective data | 50.17% |
| conversion ratio | 97.18% |
| methylation ratio | 84.20% |

6. Amount of Repetitive Sequences in the Library as Compared to the Sanger Sequencing Method The sequences aligned to genome in the data of 45 cycle Paired End sequencing were subjected to higher biological information analysis. The results (Table 9) showed that the amount of the repetitive sequences was 30.87%, which was reduced by more than half relative to the amount of repetitive sequences (75%) of MeDIP detected by Sanger sequencing method. The results demonstrated that a combination of MeDIP and bisulfite method had a very high specificity, and could effectively separate DNA methylated fragments from unmethylated fragments. The ratio of sequences aligned to the repetitive sequence region in the sequences by GA sequencing (30.8%), almost half of the repetitive sequences was removed. The size of sequencing library and redundant data were reduced

TABLE 9

Other parameters by GA system sequencing after YH-1 genome methylation immunoprecipitation, removal of repetitive sequences in combination with sulfonation treatment of library

| gene characteristics | data | percentage (%) |
|---|---|---|
| repetitive sequences | 2927604 | 30.83 |
| transposon | 2173324 | 22.89 |
| CpG islands | 144614 | 1.52 |
| gene elements | 1678027 | 17.66 |
| ncRNA | 24037 | |
| total number | 9493842 | |

7. Sequencing Depth Analysis of Aligned Single CpG Site by Comparing Whole Genome Sulfonation Treatment Sequencing Results with the Sequencing Results of the Present Technique As to 1# chromosome, the sequencing results of MRERB method were compared with the results of whole genome bisulfite treatment, and the comparison of sequencing depth of commonly aligned CpG site in genomic functional region showed that the sequencing depth tendency of both was substantially consistent (see FIG. 10), while there was a difference by 4 times in sequencing depth. Thus, only 10 G data were needed for the MRERB method of the present invention to arrive at level of 70 G data of whole genome bisulfite sequencing, and whole data quantity was reduced by 7 times.

Therefore, the primary analysis of Solexa sequencing data by MRERB library preparation technique demonstrated that the method can specifically separate methylated DNA fragments from the whole genome and remove a majority of repetitive sequences there from. After bisulfite treatment, the sequences read by GA system can be aligned and localized, and methylation analysis of single cytosine can be carried out. The method can be used to detect methylation of different samples.

To sum up, the present technique can detect DNA methylation in functional region of genome and precisely align methylation status of single cytosine. Under the methylation sequencing data are saturated in the functional region, the data amount is reduced by 80-90% relative to the data of whole genome bisulfite sequencing, and detecting cost for each sample is lowered by 70-80%.

---

What is claimed is:

1. A method for constructing a methylated DNA library, consisting of:
   A) fragmenting a DNA sample;
   B) ligating auxiliary adapters to the ends of the fragmented DNA obtained in A);
   C) enriching methylated DNA fragments;
   D) removing fragments comprising moderately and highly repetitive sequences from the DNA fragments obtained in C);
   E) converting unmethylated cytosines in the product obtained in D) into uracils by bisulfite treatment;
   F) amplifying the DNA obtained in E) with primers; and
   G) removing the auxiliary adapters by digesting the product obtained in step F) with a restriction enzyme, wherein for step B), the ends of the auxiliary adapters that link to the fragmented DNA are joining ends, the other ends are non-joining ends, and the auxiliary adapters are selected from at least one of the following a-d:
   a) an adapter that is free of restriction enzyme cutting sites and has a non-joining end that is an overhang structure and a joining end that is a blunt end;
   b) an adapter that is free of restriction enzyme cutting sites and has a non-joining end that is a forked structure and a joining end that is a blunt end;
   c) an adapter that is free of restriction enzyme cutting sites and has a non-joining end that is an overhang structure and a joining end that is a sticky end; or
   d) an adapter that is free of restriction enzyme cutting sites and has a non-joining end that is a forked structure and a joining end that is a sticky end;
   and wherein (i) the primers in step F) are complementary to the sequence of the auxiliary adapters after conversion in step E) and have a restriction enzyme recognition site near the 5' end, (ii) the cutting sites for said restriction enzyme are located within five base pairs downstream of the linking site of the auxiliary adapters to the fragmented DNA, and (iii) step G) is carried out using a single restriction enzyme with a recognition site that corresponds to the restriction enzyme recognition site contained in the primers.

2. A method for sequencing methylated DNA, consisting of:
   A) fragmenting a DNA sample;
   B) ligating auxiliary adapters to the ends of the fragmented DNA obtained in A);
   C) enriching methylated DNA fragments;
   D) removing moderately and highly repetitive sequences from the product obtained in C);

E) converting unmethylated cytosines in the product obtained in D) into uracils by bisulfite treatment;
F) amplifying the DNA obtained in E) with primers;
G) removing the auxiliary adapters by digesting the product obtained in step F) with a restriction enzyme; and
H) sequencing the DNA obtained in G);
optionally, comprising aligning the sequencing results of H) with the sequence of sample DNA or a reference sequence to identify the numbers and positions of methylated cytosine bases;
wherein in step B), the ends of the auxiliary adapters that link to the fragmented DNA are joining ends, the other ends are non-joining ends, and the auxiliary adapters are selected from at least one of the following a-d:
a) an adapter that is free of restriction enzyme cutting sites and has a non-joining end that is an overhang structure and a joining end that is a blunt end;
b) an adapter that is free of restriction enzyme cutting sites and has a non-joining end that is a forked end and a joining end that is a blunt end;
c) an adapter that is free of restriction enzyme cutting sites and has a non-joining end that is an overhang structure and a joining end that is a sticky end; or
d) an adapter that is free of restriction enzyme cutting sites and has a non-joining end that is a forked structure and a joining end that is a sticky end;
and wherein (i) the primers in step F) are complementary to the sequence of the auxiliary adapters after conversion in step E) and have a restriction enzyme recognition site near the 5' end, (ii) the cutting sites for said restriction enzyme are located within five base pairs downstream of the linking site of the auxiliary adapters to the fragmented DNA, and (iii) step G) is carried out using a single restriction enzyme with a recognition site that corresponds to the restriction enzyme recognition site contained in the primers.

3. The method of claim 1 or 2, wherein step A) comprises:
a) fragmenting genomic DNA into DNA fragments;
b) end repairing the DNA fragments obtained in step a) to obtain DNA fragments with blunt ends; and
c) adding an "A" base to the 3'-end of the DNA fragments obtained in step b).

4. The method of claim 1, wherein step G) further comprises: end repairing the DNA without auxiliary adapters and ligating sequencing adapters to the DNA after end repairing.

5. The method according to claim 1 or 2, wherein step C) is performed by the MeDIP technique or the MBD technique.

6. The method according to claim 1 or 2, wherein step D) is performed by hybridization based on Cot-1 DNA binding.

7. The method according to claim 1 or 2, wherein the auxiliary adapters are each labeled at the 5'-end with a biotin.

* * * * *